United States Patent [19]  [11] 4,186,001
Foley  [45] Jan. 29, 1980

[54] PHOTOGRAPHIC PRODUCTS AND PROCESSES EMPLOYING A 3,3 DISUBSTITUTED SULFAM(NA)PHTHALEIN FILTER DYE

[75] Inventor: James W. Foley, Andover, Mass.

[73] Assignee: Polaroid Corporation, Cambridge, Mass.

[21] Appl. No.: 957,161

[22] Filed: Nov. 2, 1978

[51] Int. Cl.$^2$ .................. G03C 1/40; G03C 1/84; G03C 7/00; G03C 5/54
[52] U.S. Cl. ..................... 430/220; 430/229
[58] Field of Search .............. 96/3, 29 D, 76 R, 77, 96/29R, 73, 74, 84 R, 112, 66 R, 63, 21, 22

[56] References Cited
U.S. PATENT DOCUMENTS 3,560,214 2/1971 Ruda .................. 96/84 R
3,647,437 3/1972 Land .................. 96/84 R Primary Examiner—Richard L. Schilling
Attorney, Agent, or Firm—Sybil A. Campbell

[57] ABSTRACT

The present invention is concerned with photographic products and processes, particularly diffusion transfer products and processes employing as a colored light-screening dye(s), a 3,3-disubstituted sulfam(na)phthalein wherein one of the 3-substituents is a 4'-hydroxy-1'-naphthyl moiety substituted in the 3'-position with a perhalomethylcarbinol group and the other of the 3-substituents is a phenyl moiety substituted with an electron-donating group and wherein the N atom of the sulfam(na)phthalein ring is substituted with a carbonyl moiety possessing a

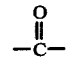

group bonded to the N atom of said sulfam(na)phthalein ring, which carbonyl moiety undergoes an irreversible cleavage reaction in alkaline solution above a predetermined alkaline pH to form a new compound which is colorless and non-reversible to said light-screening dye.

51 Claims, 2 Drawing Figures

PHOTOGRAPHIC PRODUCTS AND PROCESSES EMPLOYING A 3,3 DISUBSTITUTED SULFAM(NA)PHTHALEIN FILTER DYE

BACKGROUND OF THE INVENTION

1. Field of the Invention

This invention relates to photography, and more particularly, it relates to the use of certain sulfam(na)phthaleins derived from perhalomethylcarbinol-substituted 1-naphthols as light-screening dyes in photographic products and processes.

2. Description of the Prior Art

It is well known to use light-screening dyes in photographic elements. Such a dye may be incorporated as a filter dye in a light-sensitive emulsion layer(s) or in a layer coated over one or more light-sensitive emulsion layers or between two differently color-sensitized emulsion layers to modify the light record in the emulsion layer or to control the spectral composition of light falling on the underlying light-sensitive layer, or it may be incorporated as an antihalation dye in a non-light-sensitive layer positioned on either side of a support carrying the light-sensitive layer(s).

It is also well known that photographic films, and especially multicolor films, may and generally do vary from lot to lot, notwithstanding efforts to "repeat" previous films. Manufacturers of multicolor photographic films have developed a number of procedures to minimize the effects upon the final multicolor image of unavoidable variations in the manufacturing operations. These variations are reflected primarily in shifts in color balance as reflected in mismatching of the D log E curves of the individual red, green and blue exposures. Equipment used to coat multicolor films is highly precise but variations between intended coverage of silver halide and/or the dye image-forming materials do occur. Repeat batches of silver halide emulsions may, and usually do, vary in their photographic response. Individual layers may be dried to slightly different degrees. Films are stored for a period of time after coating to allow the films to "age", so that changes in sensitometry following coating have an opportunity to reach a plateau prior to sale. If the film is designed to be developed by a photofinisher or in a darkroom, processing of the exposed multicolor film is controlled within very narrow limits, typically within plus or minus a half degree of a prescribed temperature, in order to minimize sensitometric variations from film to film. Where the multicolor film is of the negative type, an opportunity to adjust the sensitometry occurs in printing the desired final positive image, during which operation the printing exposure may be appropriately color filtered.

The basic sources of sensitometric variations noted above exist also in multicolor diffusion transfer films, with the added complication that once the film is shipped, the sensitometric properties are essentially fixed. The opportunity for adjustment provided in darkroom processing, practically speaking, is unavailable for users of self-developing films. While professional and advanced amateur photographers may be skillful enough to utilize color correction filters to at least partially "rebalance" the color balance, ordinary users of the film would only be confused by such additional operations.

Commonly, assigned copending U.S. Patent application Ser. No. 537,124 of Edwin H. Land filed Dec. 30, 1974 is concerned with modifying the sensitometric properties of multicolor diffusion transfer film units to achieve the requisite color correction. This is accomplished by including a layer of a color correction filter dye(s) and effecting photoexposure therethrough, the filter dye(s) subsequent to processing being so positioned as not to contribute dye density to the multicolor transfer image, or preferably, the filter dye(s) being capable of being bleached as a result of contact with the photographic processing composition. Because the sensitometry is modified after the photosensitive element has been coated but prior to packaging of the film, the user is unaware of, and not involved in, the corrective action.

The dyes employed for this and other light-screening purposes, in addition to having the requisite spectral absorption characteristics for their intended use, should be photochemically inert, that is, they should not have any adverse effect on the properties of the light-sensitive emulsion layer(s), and preferably, should be capable of being permanently decolorized so as not to leave stain in association with the final image of the processed photographic element. In photographic processes where the light-screening dye is removed by being dissolved in a processing solution, it is usually preferred that the dye also decolorize in order to avoid contamination of the processing solution and to prevent staining from residual dye in the processed film unit.

Though various classes of dyes have been proposed for use in antihalation, color correction and other filter layers, the dyes heretofore employed have not been altogether satisfactory. Some of the dyes tend to reduce sensitivity, fog or exert other adverse effect on the light-sensitive material. However, the major drawback of previously employed dyes is their tendency to impart stain to the final image due to incomplete decolorization or reversal of some of the decolorized form to the original colored form. For example, some classes of dyes rely on the presence of a reagent, such as, a sulfite for "bleaching", i.e., decolorization and unless the dyes are removed from the light-sensitive material during or after processing, their color may reappear with a reduction in sulfite concentration.

Commonly assigned copending U.S. Patent Application Ser. No. 836,006 of Stanley M. Bloom, Alan L. Borror and James W. Foley now U.S. Pat. No. 4,139,381 is directed to the use of certain 3,3-disubstituted sulfam(na)phthaleins as photographic optical filter agents and filter agent precursors. As described therein, one of the 3-substituents is a 4'-hydroxy-1'-phenyl moiety or a 4'-hydroxy-1'-naphthyl moiety, the other of the 3-substituents is a phenyl moiety or a naphthyl moiety, and the N atom of the sulfam(na)phthalein ring is substituted with a carbonyl moiety that undergoes an irreversible cleavage reaction in alkaline solution above a predetermined alkaline pH. These compounds are initially colorless, i.e., they do not absorb visible radiation intended to expose the photosensitive material but which, upon contact with an aqueous alkaline solution of base having an alkaline pH above a given value forms a colored compound capable of absorbing such radiation thereby preventing further exposure of said photosensitive material by ambient light, which colored compound after remaining in contact with said solution of base above said pH for a predetermined time forms a colorless compound as a result of the irreversible cleavage of the carbonyl moiety.

The present invention is concerned with certain sulfam(na)phthaleins derived from 2-perhalomethylcarbinol-substituted 1-naphthols which are initially colored and which find utility as photographic light-screening dyes that are free from the drawbacks associated with the dyes previously used for this purpose. The subject sulfam(na)phthalein light-screening dyes, which will be defined with greater particularity hereinafter, have a form which absorbs radiation in the visible range of 400 to 700 nm below a given alkaline pH and decolorize by undergoing an irreversible cleavage reaction with base at a pH above said alkaline pH to yield a colorless product. Because of their ability to decolorize completely and irreversibly in base above a predetermined pH without requiring a reagent, such as, a sulfite for the "bleaching" reaction and because the colorless product produced upon irreversible cleavage is inert to changes in pH, the compounds may be retained in the photographic light-sensitive element without the possibility of color reappearing in time. Besides being non-staining, the compounds are inert with respect to the light-sensitive material and thus, may be positioned in a layer adjacent to a silver halide emulsion layer or directly incorporated into an emulsion layer without having any adverse effect on the properties of the emulsion.

SUMMARY OF THE INVENTION

It is, therefore, the primary object of the present invention to provide photographic products and processes which employ as a light-screening dye(s) certain 3,3-disubstituted sulfam(na)phthaleins wherein one of the 3-substituents is derived from a perhalomethylcarbinol-substituted 1-naphthol, which class of light-screening dyes become decolorized when contacted with an alkaline photographic processing composition.

It is another object of the present invention to provide photographic multicolor diffusion transfer film units which contain a layer of said sulfam(na)phthalein dye(s) so positioned that photoexposure is effected therethrough to correct imbalances in the color sensitometry of the multicolor photosensitive element of said film units.

Other objects of this invention will in part be obvious and will in part appear hereinafter.

This invention accordingly comprises the process involving the several steps and the relation and order of one or more of such steps with respect to each of the others and the products and compositions possessing the features, properties and the relation of elements which are exemplified in the following detailed disclosure, and the scope of the application of which will be indicated in the claims.

For a fuller understanding of the nature and objects of the present invention, reference should be had to the following detailed description taken in conjunction with the accompanying drawings.

DETAILED DESCRIPTION OF THE INVENTION

Figure 1:
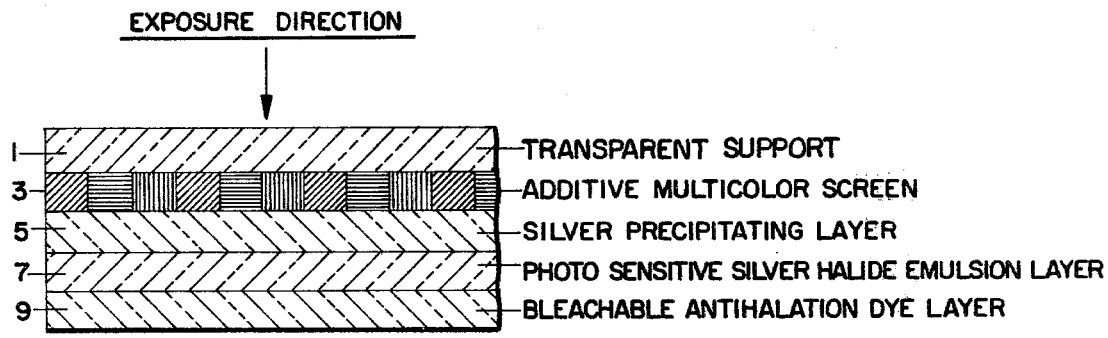
FIG. 1 is a diagrammatic, enlarged cross-sectional view of a diffusion transfer film unit incorporating a light-screening dye of the present invention as a bleachable antihalation dye layer.

Specifically, the compounds employed as light-screening dyes in accordance with the present invention may be represented by the formula

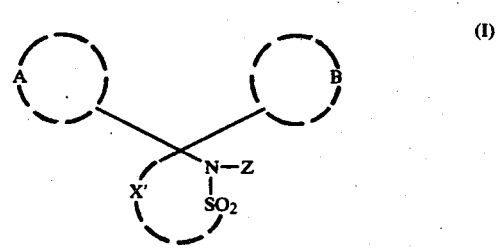

(I)

wherein A is a 4'-hydroxy-1'-naphthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol. Preferably, the B moiety is sufficiently electron donating to give a compound which additionally has a λmax greater than 550 nm as measured in trifluoroethanol.

The halo substituents of said perhalomethyl are preferably fluoro and/or chloro. Preferred perhalomethyl groups include trifluoromethyl, difluoromethyl, difluorochloromethyl, dichlorofluoromethyl, dichloromethyl and trichloromethyl. When $R^I$ and $R^{II}$ both are perhalomethyl groups, they may be the same or different and usually are the same.

By "sulfamphthalein" is intended a 2,3-dihydrobenz[d]isothiazole-1,1-dioxide moiety and by "sulfamnaphthalein" is intended a 2,3-dihydronaphtho[1,8-de]-1,2-thiazine-1,1-dioxide moiety. The respective 2,3-dihydrobenz[d]isothiazole-1,1-dioxide and 2,3-dihydronaphtho[1,8-de]-1,2-thiazine-1,1-dioxide ring-closing moieties are illustrated below:

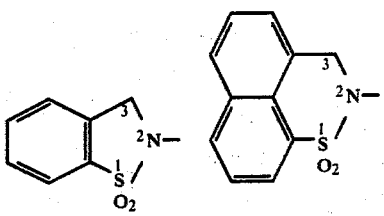

Besides being substituted with one or more electron-donating substituents, the phenyl moiety comprising B may contain substituents that are not electron-donating provided that the overall electron donating properties of the B moiety are sufficient to meet the criterion of giving a compound having an epsilon of at least 4000 in the visible wavelength range, i.e., 400 to 700 nm. By an electron-donating substituent is meant a substituent having a negative sigma value as defined by Hammett's Equation. Typical electron-donating substituents include -N,N-(dialkyl)amino, pyrrolidino and fused substituents, e.g., a fused [ij]quinolizidine ring.

It will be understood that the A moiety and/or the ring-closing moiety of the compounds represented in formula I above also may contain one or more substituents in addition to those specified, which substituents should not interfere with the intended use of the compounds.

Typical substituents include branched or straight chain alkyl, such as, methyl, ethyl, isopropyl, n-butyl, t-butyl, hexyl, octyl, dodecyl, hexadecyl, octadecyl and eicosanyl; aryl, such as phenyl and naphthyl; alkaryl and aralkyl, preferably, alkyl-substituted phenyl and phenyl-substituted alkyl, such as p-ethylphenyl, p-octylphenyl, p-dodecylphenyl, benzyl, phenethyl, phenylhexyl and phenyldodecyl; alkoxy, such as, methoxy, ethoxy, butoxy, octadecyloxy, 1-ethoxy-2-(β-ethoxyethoxy); aryloxy, such as, phenoxy, benzyloxy and naphthoxy; alkoxyalkyl, such as, methoxymethyl, ethoxymethyl, and dodecyloxyethyl; halo, such as, fluoro, bromo and chloro; trihalomethyl, such as, trifluoromethyl and trichloromethyl; sulfonamido (—NH—SO$_2$R° wherein R° is alkyl, aryl, alkaryl or aralkyl); sulfamoyl (—SO$_2$—NH—R° wherein R° has the same meaning given above); acyl

wherein R° has the meaning given above); sulfonyl (—SO$_2$R° wherein R° has the same meaning given above); sulfo, cyano; carboxy; hydroxy; an amino including mono- and disubstituted amino (—NR'R" wherein R' and R" each are hydrogen, alkyl, aryl, alkaryl or aralkyl).

As discussed above, Z is a carbonyl moiety containing a

group bonded to the N atom of said ring-closing moiety that undergoes an irreversible cleavage reaction in alkaline solution above a predetermined alkaline pH. Examples of mechanisms by which cleavage may occur are alkaline hydrolysis or an elimination reaction, e.g., E$_1$ or E$_2$ elimination. Illustrative Z moieties include

—CR wherein R is methyl substituted with one halo group selected from chloro, bromo and fluoro or substituted with two of said halo groups, preferably the same; phenoxy substituted with one or more electron-withdrawing groups, one of said groups being substituted in the para position; and preferably, —O(CH$_2$)$_2$Y wherein Y is an electron-withdrawing group.

Preferred light-screening dyes of the present invention are those of the formula

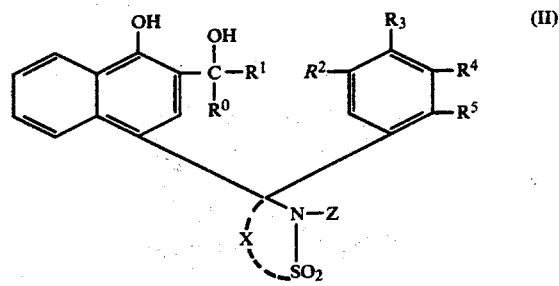

wherein R$^0$ is perhalomethyl selected from trifluoromethyl, difluoromethyl, difluorochloromethyl, dichlorofluoromethyl, dichloromethyl and trichloromethyl; R$^1$ is selected from hydrogen and perhalomethyl having the same meaning given above; R$^2$ and R$^4$ each are selected from hydrogen, alkyl, alkoxy, chloro and fluoro; R$^5$ is hydrogen, hydroxy, alkyl or alkoxy; R$^3$ is pyrrolidino, -N,N-(dialkyl)amino, -N,N-(w-R$^6$-alkyl)$_2$amino wherein R$^6$ is halo, preferably chloro, or hydroxy; R$^2$, R$^3$ and R$^4$ taken together represent the atoms necessary to complete a fused [ij]-quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and Z is $$\overset{O}{\underset{\|}{-CO(CH_2)_2Y}}$$

wherein Y is an electron-withdrawing group.

By electron-withdrawing group is meant a group having a positive sigma value as defined as Hammett's Equation. Preferably, Y is an electron-withdrawing group having a positive sigma value greater than 0.60. Preferred electron-withdrawing groups include nitro; cyano; —SO$_2$CH$_3$;

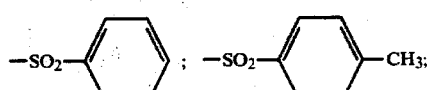

—COCH$_3$; and —SO$_2$N(CH$_2$Ph)$_2$. The sigma value for these and other groups have been reported by Eugen Muller, Methoden Der Organischen Chemie, Georg Thieme Verlag, Stuttgart, 1970, p. 78.

Usually, the alkyl and alkoxy substituents comprising R$^2$, R$^4$ and R$^5$ are lower alkyl having 1 to 4 carbon atoms, such as, methyl, ethyl, n-propyl, isopropyl, s-butyl and n-butyl and lower alkoxy having 1 to 4 carbon atoms, such as, methoxy, ethoxy, propoxy and butoxy. Also, the alkyl groups of the -N,N-(dialkyl)amino each are usually alkyl having 1 to 4 carbon atoms and similarly, the alkyl groups of the -N,N-(w-R⁶-alkyl)₂amino usually contain 1 to 4 carbon atoms.

In a particularly preferred embodiment, X in formula (II) above represents the atoms necessary to complete 2,3-dihydrobenz[d]isothiazole-1,1-dioxide.

Specific examples of light-screening dyes within the scope of the present invention are as follows:

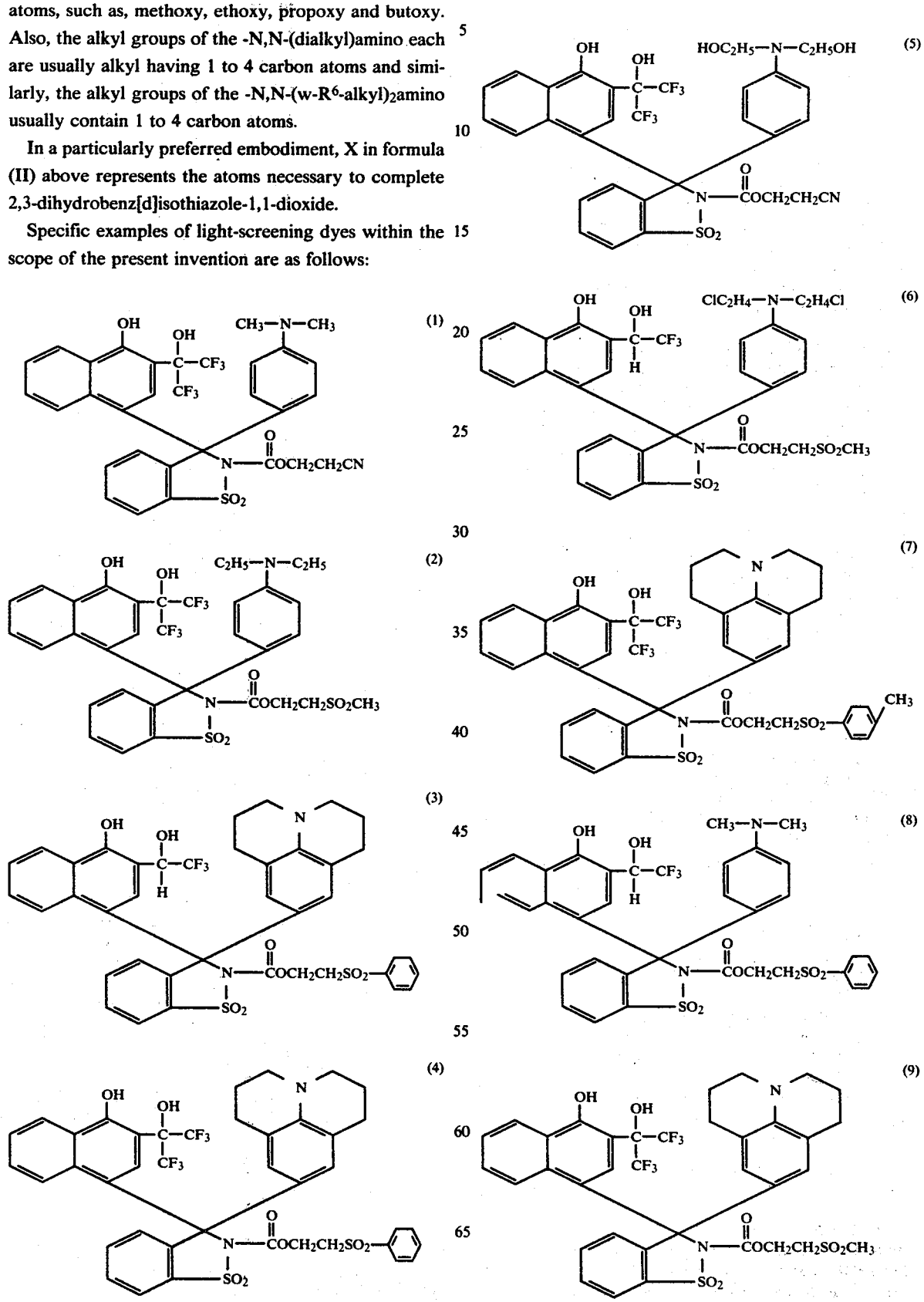

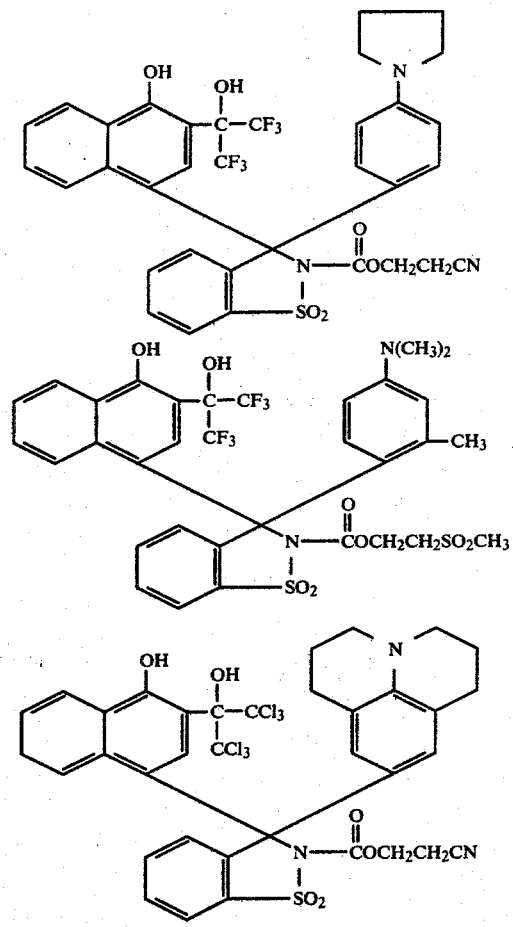

One method of synthesizing the compounds of the present invention comprises reacting (a) a carbocyclic aryllithium compound selected from a 4-OLi-naphthyllithium compound substituted in the 3-position with a group,

wherein $R^I$ is perhalomethyl and $R^{II}$ is hydrogen or perhalomethyl and a 4-OLi-phenyllithium compound substituted in the 3-position with a group,

wherein $R^I$ is perhalomethyl and $R^{II}$ is hydrogen or perhalomethyl and (b) a compound selected from a 3-substituted-benz[d]isothiazole-1,1-dioxide wherein said 3-substituent is a phenyl moiety or a naphthyl moiety provided said 3-substituent is a phenyl moiety when said carbocyclic aryllithium compound is said 4-OLi-naphthyllithium compound and a 3-substituted-naphtho[1,8-de]1,2-thiazine-1,1-dioxide wherein said 3-substituent is a phenyl moiety or a naphthyl moiety provided said 3-substituent is a phenyl moiety when said carbocyclic aryllithium compound is said 4-OLi-naphthyllithium compound to give (c) a 3,3-disubstituted-2,3-dihydrobenz[d]isothiazole-1,1-dioxide or a 3,3-disubstituted-2,3-dihydronaphtho[1,8-de]-1,2-thiazine-1,1-dioxide wherein one of the 3,3-substituents is a 4'-OH-1'-naphthyl moiety substituted in the 3'-position with

wherein $R^I$ and $R^{II}$ have the same meaning given above or a 4'-OH-1'-phenyl moiety substituted in the 3'-position with

wherein $R^I$ and $R^{II}$ have the same meaning given above and the other of the 3,3-substituents is a phenyl moiety or a naphthyl moiety.

The 3-substituted-benz[d]isothiazole-1,1-dioxides reacted with the "lithiated" phenol (or 1-naphthol) reagent may be a 3-(4'-OP-1'-phenyl/4'-OP-1'-naphthyl)-benz[d]isothiazole-1,1-dioxide or a 3-(phenyl/naphthyl)benz[d]isothiazole-1,1-dioxide wherein the 3-(phenyl/naphthyl) substituent may be unsubstituted or substituted with other than a 4'-OP substituent. It will be understood that the corresponding 3-substituted naphtho[1,8-de]-1,2-thiazine-1,1-dioxides also may be reacted with the "lithiated" reagent.

When 3-(4'-OP-1'-phenyl/4'-OP-1'-naphthyl)-benz[d]isothiazole-1,1-dioxides are employed as starting materials in this method, they are prepared by blocking the functional hydroxy group and any substituent group(s), as may be appropriate, of the selected 4-halophenol or 4-halo-1-naphthol and converting the blocked phenol or 1-naphthol to the corresponding Grignard or lithium reagent which is then reacted with a saccharin reagent. The 4-halo substituent may be chloro, bromo or iodo when the lithium reagent is prepared by reacting the blocked phenol or blocked 1-naphthol with lithium metal and is either bromo or iodo when the lithium reagent is made via a lithium exchange reaction using, for example, n-butyllithium. In preparing the Grignard reagent by reacting the blocked phenol or 1-naphthol with magnesium metal, the 4-halo substituent may be chloro, bromo or iodo. The Grignard or lithium reagent thus prepared is then reacted with saccharin, the N-lithium salt of saccharin or saccharin pseudo-chloride to yield the corresponding 3-(4'-OP-1'-phenyl/4'-OP-1'-naphthyl)benz[d]isothiazole-1,1-dioxide. Generally, the Grignard reagent is reacted with the pseudo-chloride, and the lithium reagent is reacted with the N-lithium salt. The 3-(4'-OP-1'-phenyl/4'-OP-1'-naphthyl)naphtho[1,8-de]-1,2-thiazine-1,1-dioxides may be prepared in a similar manner by reacting the Grignard or lithium reagent with 2,3-dihydro-3-oxo-naphtho[1,8-de]-1,2-thiazine-1,1-dioxide, its pseudo-chloride or the N-lithium derivative thereof.

The groups selected for protecting the functional phenolic or naphtholic hydroxy group and other hydroxy groups that may be present in the phenol or 1- naphthol should be stable to and compatible with organolithium and Grignard reagents and should protect the hydroxy group(s) against reaction under the conditions encountered in preparing the starting materials. It will be appreciated that starting materials without protecting groups on the 3-(4'-OH-1'-phenyl/4'-OH-1'-naphthyl) moiety may be employed in the subsequent acylation reactions. However, it is more convenient to leave the protecting group(s) on the starting materials derived from the 3-(4'-OP-1'-phenyl/4'-OP-1'-naphthyl)benz[d]isothiazole-1,1-dioxides and remove the protecting groups subsequent to the acylation reaction. Thus, the protecting group selected should be capable of being easily removed under weakly acid conditions to regenerate the hydroxy group(s) without the removal of or adversely affecting the N-substituent or other substituents that may be present. Alkyl groups, such as methyl and ethyl, may be employed in those instances where they can be removed without removal of the N-substituent. Because they can be readily removed without disturbing the N-substituent or other substituents, the phenol or 1-naphthol preferably is protected with methoxymethyl, 2'-tetrahydropyranyl or dimethyl-t-butylsilyl. The blocked phenols and 1-naphthols employing these protecting groups may be prepared by methoxymethylation as described, for example, by Kaoru Fuji et al, *Synthesis*, 4, pp. 276–277 (1975), by tetrahydropyranylation as described, for example, by William E. Parham et al, *J. Amer. Chem. Soc.*, 70, pp. 4187–4189 (1948) or by silylating with dimethyl-t-butylsilyl chloride in the presence of imidazole as described by E. J. Corey et al, *J. Amer. Chem. Soc.*, 94, pp. 6190–6191 (1972).

When the starting materials are 3-(phenyl/naphthyl)-benz[d]isothiazole-1,1-dioxides, i.e., other than 3-(phenyl/naphthyl) compounds containing a 4'-OP substituent, they may be prepared in a similar manner by blocking hydroxy and/or other substituent group(s), as may be appropriate, of the selected halo-benzene or halo-naphthalene compound and converting the halo compound to the corresponding Grignard or lithium reagent which is then reacted with the saccharin reagent to give the corresponding 3-substituted-benz[d]isothiazole-1,1-dioxide.

Certain 3-(4'-OP-1'-phenyl/4'-OP-1'-naphthyl)benz[d]isothiazole-1,1-dioxides form the subject matter of copending U.S. Patent Application Ser. No. 836,024 of Alan L. Borror, L. Cincotta, E. W. Ellis, J. W. Foley and M. M. Kampe filed Sept. 23, 1977. 3-(Phenyl/naphthyl)benz[d]isothiazole-1,1-dioxides substituted with certain N-heterocyclic moieties form the subject matter of copending U.S. Patent Application Ser. No. 836,022 of Alan L. Borror, J. W. Foley and J. W. Lee, Jr. filed Sept. 23, 1977, and 3-(9'-julolidinyl)benz[d]isothiazole-1,1-dioxide forms the subject matter of copending U.S. Patent Application Ser. No. 836,023 also filed Sept. 23, 1977.

The "lithiated" derivative of the perhalomethylcarbinol-substituted phenol or 1-naphthol is prepared by reacting the selected 4-halophenol or 4-halo-1-naphthol with at least three molar equivalents of lithium metal or preferably n-butyllithium as illustrated below

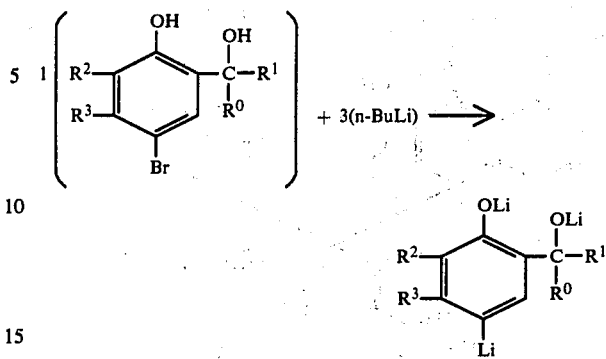

The perhalomethylcarbinol-substituted phenols and 1-naphthols may be prepared according to the procedures set forth by Basil S. Farah et al, *J. Org. Chem.*, Vol. 30, p. 1003 (1965) and are halogenated in any conventional manner to give the 4-halo derivatives, for example, by reacting the perhalomethylcarbinol-substituted compound with chloride or bromine, with or without a catalyst; N-bromosuccinimide or iodinemonochloride.

In carrying out the synthesis, the selected 3-substituted-benz[d]isothiazole-1,1-dioxide is reacted with at least one molar equivalent of the "lithiated" phenol or 1-naphthol in an inert organic solvent, such as, benzene, diethyl ether, dioxane, hexane, toluene, petroleum ether or tetrahydrofuran. The reactants may be employed in equivalent, i.e., equimolar amounts but ordinarily an excess of about 0.1 to 1.0 mole of the "lithiated" phenol or 1-naphthol is employed per 1.0 mole of the 3-substituted-benz[d]isothiazole-1,1-dioxide. The reaction temperature may vary over a relatively wide range from about −80° to 50° C. as may be readily determined for the particular reactants. For achieving maximum yields, the reaction generally is conducted at a temperature below about 0° C. and preferably between about −65° C. and −25° C. As a matter of convenience, the 4-halo perhalomethylcarbinol-substituted phenol or 1-naphthol is reacted with the requisite amount of n-butyllithium at reduced temperatures of about −50° to −70° C. in an inert organic solvent such as those enumerated above to give the corresponding "lithiated" derivative and then the 3-substituted-benz[d]isothiazole-1,1-dioxide is added without isolating the "lithiated" derivative.

To prepare the

compounds, the selected 3,3-disubstituted-2,3-dihydrobenz[]isothiazole-1,1-dioxide as prepared above is reacted with at least one molar equivalent of an acid halide of the formula

wherein W is chloro or bromo and Y has the same meaning given above in pyridine solution to give the corresponding

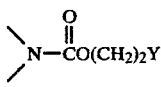

compound. About 1 to 6 moles of acid halide may be used for each mole of the 3,3-disubstituted-2,3-dihydrobenz[d]isothiazole-1,1-dioxide, and usually 5 to 6 moles are employed. Since the reaction is exothermic, external heating is initially unnecessary, but the reaction mixture may be heated to facilitate completion of the reaction, if desired. Ordinarily, the reaction temperature ranges between about 0° and 100° C., and, if desired, the reaction may be conducted in an inert atmosphere, for example, under nitrogen. Preferably, the acylation reaction is conducted in the presence of acidic alumina or a zeolite molecular sieve. The amount of acidic alumina and molecular sieve may be readily determined empirically, and ordinarily, about 2 to 20 g of the alumina or molecular sieve per gram of 3,3-disubstituted-2,3-dihydrobenz[d]isothiazole-1,1-dioxide is sufficient to give the desired

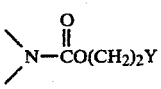

compound as the major or exclusive reaction product, i.e., with little or no derivatization of the hydroxy groups.

The carboxylic acid halides may be prepared by reacting the selected $HO(CH_2)_2Y$ with phosgene to give the corresponding

It will be appreciated that any protecting group, P, as may be present are removed subsequent to the acylation step by treating the N-acylated compound with acid having a pH between about 0.1 and 5.0 at a temperature between about 20° and 100° C. The acid may be an inorganic acid, such as, hydrochloric acid or sulfuric acid in a protic solvent, e.g., water, alkanol, such as, methanol or ethanol, or aqueous alkanol, or the acid may be an organic acid, such as, acetic acid or trifluoroacetic acid alone or in a protic solvent, such as those mentioned above.

The method of reacting the "lithiated" perhalomethylcarbinol-substituted phenol or 1-naphthol and the 3-(substituted)benz[d]isothiazole-1,1-dioxide to give the 3,3-disubstituted intermediate forms the subject matter of commonly assigned copending U.S. Patent Application Ser. No. 956,908 of Louis Cincotta and James W. Foley filed concurrently herewith. The method of reacting the aforementioned 3,3-disubstituted-2,3-dihydrobenz[d]isothiazole-1,1-dioxide intermediates with

to give the corresponding

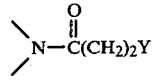

compounds forms the subject matter of commonly assigned copending U.S. Patent Application Ser. No. 957,162 of Louis Cincotta and James W. Foley also filed concurrently herewith. For convenience, the specifications of aforementioned applications Ser. Nos. 956,908 and 957,162 are specifically incorporated herein.

The compounds of the present invention also may be prepared according to the method disclosed and claimed in commonly assigned copending U.S. Patent Application Ser. No. 836,010 of Stanley M. Bloom, Alan L. Borror and James W. Foley filed Sept. 23, 1977, by reacting a 3,3-disubstituted-2,3-dihydrobenz[d]isothiazole-1,1-dioxide wherein one of the 3-substituents is (4'-OP-1'-phenyl/4'-OP-1'-naphthyl) possessing

in the 3'-position and a carboxylic acid halide, e.g.,

wherein W is chloro or bromo and R has the same meaning given above to give the corresponding N-carbonyl derivative followed by removing the protecting group(s), P, with dilute acid to yield the product compounds. The 3,3-disubstituted-2,3-dihydrobenz[d]isothiazole-1,1-dioxides employed in the foregoing method may be prepared by reacting a 3-(4'-OP-1'-phenyl/4'-OP-1'-naphthyl)benz[d]isothiazole-1,1-dioxide possessing

in the 3'-position and a phenyllithium or a naphthyllithium reagent as disclosed and claimed in commonly assigned copending U.S. Patent Application Ser. No. 836,008 of Alan L. Borror, Louis Cincotta, James W. Foley and Marcis M. Kampe filed Sept. 23, 1977, or by reacting a 3-(phenyl/naphthyl)benz[d]isothiazole-1,1-dioxide and a 4'-OP-phenyllithium/4'-OP-naphthyllithium compound possessing

in the 3'-position to give the corresponding 3,3-disubstituted-2,3-dihydrobenz[d]isothiazole-1,1-dioxide as disclosed and claimed in commonly assigned copending U.S. Patent Application Ser. No. 836,025 of Alan L. Borror, James W. Foley, Marcis M. Kampe and John W. Lee, Jr., also filed Sept. 23, 1977. The protecting groups, P, may be those enumerated above, but preferably, in blocking the perhalomethylcarbinol-substituted phenols and 1-naphthols, groups, such as, benzyl are employed. The 3-substituted-benz[d]isothiazole-1,1-dioxides employed as starting materials in aforementioned applications Ser. Nos. 836,008 and 836,025 are prepared as described above.

The carboxylic acid halides are well known and may be prepared in a conventional manner, for example, by reacting the selected carboxylic acid, RCOOH, with phosphorus trichloride, phosphorus pentachloride or thionyl chloride to give the corresponding RCOCl, or by reacting the selected ROH with phosgene to give the corresponding ClCOOR.

EXAMPLE 1

Preparation of the compound having the formula

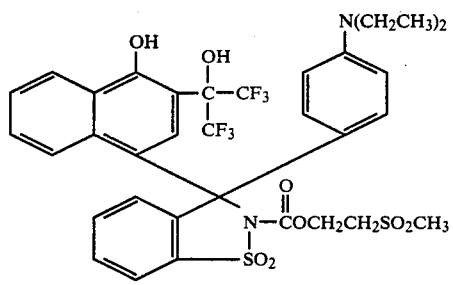

(a) 4-Bromo-2-(α-hydroxy-α-trifluoromethyl-β,β,β-trifluoroethyl)-1-naphthol (1.0 g) was dissolved in 25 ml tetrahydrofuran at room temperature under nitrogen, then cooled to −65° C. To this solution was added dropwise 3.21 ml of butyllithium (2.4 M in hexane). The resulting solution was stirred for one hour at −65° C. and then 3-(4′-N,N-diethylamino-1′-phenyl)benz[d]isothiazole-1,1-dioxide (0.51 g) was added, the solution warmed to −20° C., then cooled back to −65° C. and stirred for one hour. TLC on silica gel with ether showed that the reaction was complete. The reaction solution was poured into 200 ml. of water, the pH adjusted to 6 with conc. HCl and the resulting solution extracted with ether The ether layer was separated and washed with 200 ml. of 1 N sodium hydroxide. The aqueous sodium hydroxide layer was separated, washed well with ether, then neutralized with conc. HCl and extracted with ether. The ether extract was dried over anhydrous sodium sulfate and evaporated to give 3-[(-3′-α-hydroxy-α-trifluoromethyl-β,β,β-trifluoroethyl)-4′-hydroxy-1′-naphthyl]-3-[4′-N,N-diethylamino-1′-phenyl]-2,3-dihydrobenz[d]isothiazole-1,1-dioxide as a green solid (0.82 g; 50% yield).

(b) The compound prepared in step (a) above (0.7 g) was dissolved in 25 ml pyridine at room temperature. To this was added 0.21 g of ClCOOCH₂CH₂SO₂CH₃ and the reaction mixture stirred for several hours. TLC on silica gel with ether indicated no apparent reaction. Thus, additional acid halide (0.42 g) was added and the mixture stirred overnight. The reaction mixture was poured into water, extracted with ether and the ether extract evaporated. The title compound was obtained as a blue compound from the ether residue by preparative TLC on silica gel.

The 3-(4′-N,N-diethylamino-1′-phenyl)benz[d]isothiazole-1,1-dioxide was prepared as follows:

4-Bromo-N,N-diethylaniline (22.8 g) was dissolved in 100 ml. of anhydrous tetrahydrofuran under nitrogen and then cooled to −74° C. To this solution was added dropwise 41.8 ml of n-butyllithium (2.4 M in hexane) over a 50-minute period. (The temperature was maintained at −70° C. during the addition.) The solution was stirred for one hour. Then a solution of the N-lithium salt of saccharin in 100 ml of tetrahydrofuran was added dropwise to the aniline solution at −70° C. using a double ended needle. The resulting reaction mixture was stirred for 4 hours, poured slowly into 1 liter of water and the pH adjusted to 6 with conc. HCl. An orange precipitate formed which was filtered, dried and dissolved in 250 ml of methanol containing about 5 ml of conc. HCl. The solution was refluxed for 30 minutes and the precipitate collected to give 14.0 g of the title compound (melting range 207°–208° C.).

EXAMPLE 2

Preparation of the compound having the formula

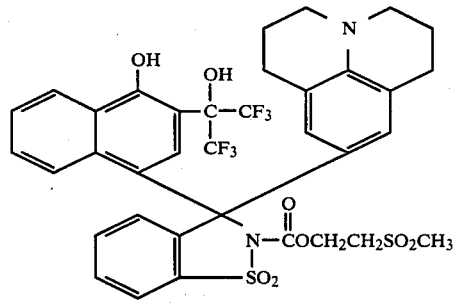

(a) 3-[(3′-α-hydroxy-α-trifluoromethyl-β,β,β-trifluoroethyl)-4′-hydroxy-1′-naphthyl]-3-(9′-julolidinyl)-2,3-dihydrobenz[d]isothiazole-1,1-dioxide was prepared according to the procedure given in Example 1 above except that 3-(9′-julolidinyl)benz[d]isothiazole-1,1-dioxide and 4-bromo-2-(α-hydroxy-α-trifluoromethyl-β,β,β-trifluoroethyl)-1-naphthol were employed in step (a).

(b) The compound prepared in step (a) (17.0 g) was dissolved in 400 ml of pyridine at room temperature under nitrogen. To this solution was added ½ pound of Type 3A molecular sieves. This was stirred mechanically in the dark and 30 g of β-(methylsulfonyl)ethylchloroformate was added and stirred for 3 hours. TLC on silica gel with 1:9 methanol/ether showed a trace of the starting isothiazole. The reaction mixture was filtered, washed with methylene chloride, poured into 5 liters of water and extracted with 1500 ml of methylene chloride. The methylene chloride was dried over sodium sulfate and evaporated under reduced pressure to remove all of the pyridine. The residue was washed with hexane several times and then vacuum dried to give 21.0 g of the title compound as a blue solid.

EXAMPLE 3

Preparation of the compound of the formula

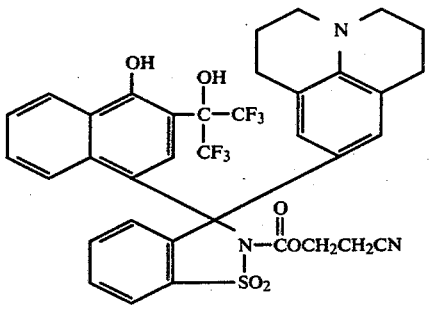

(a) 3-[(3'-α-hydroxy-α-trifluoromethyl-β,β,β-trifluoroethyl)-4'-hydroxy-1'-naphthyl]-3-(9'-julolidinyl)-2,3-dihydrobenz[d]isothiazole-1,1-dioxide was prepared according to the procedure given in Example 1 above except that 3-(9'-julolidinyl)benz[d]isothiazole-1,1-dioxide and 4-bromo-2-(α-hydroxy-α-trifluoromethyl-β,β,β-trifluoroethyl)-1-naphthol were employed in step (a).

(b) The compound prepared in step (a) (1.5 g) was dissolved in 25 ml of pyridine; 3 g of acidic alumina was added; and then 1.0 ml of β-cyanoethylchloroformate was added. The resulting reaction mixture was stirred for 16 hours at room temperature. The yellow solution turned green to cyan. The alumina was removed from the pyridine by filtration. The filtrate was poured into 200 ml of water, extracted with ether and the ether dried over sodium sulfate and evaporated. The residue was purified by medium pressure column chromatography using a silica gel stationary phase and 5% methanol in methylene chloride as elutant. TLC of samples on silica gel with ether showed the title compound as a fairly pure product.

The 3-(9'-julolidinyl)benz[d]isothiazole-1,1-dioxide was prepared as follows:

(a) 134 g (0.758 mol) of 98% julolidine was dissolved in 500 ml of glacial acetic acid. To this solution was added a solution of 121 g (0.758 mol) of bromine in 2400 ml of glacial acetic acid. After the addition, the reaction mixture was stirred for 15 minutes and then tested for excess bromine using KI paper. More bromine was added until an excess was detected. The reaction mixture was then stirred for 1 hour at room temperature. The pink solid which formed was collected and washed several times with ether and dried in a vacuum oven overnight to give 245 g of the hydrobromide salt of 9-bromojulolidine. Yield 92% by weight.

(b) 75 g (0.22 mol) of 9-bromojulolidine hydrobromide prepared in step (a) was suspended in 1200 ml of ether. To the suspension was added 650 ml of 1 N sodium hydroxide and the mixture stirred for 5-10 minutes. The two layers were separated and the aqueous layer was extracted with 1000 ml of ether. The organic layers were combined, dried over anhydrous calcium sulfate and the ether evaporated to yield 51.97 g (0.206 mol) of 9-bromojulolidine as a dark oil.

(c) The 9-bromojulolidine was dissolved in 400 ml of dry tetrahydrofuran under nitrogen at −65° C. 85.8 ml of n-butyllithium (2.4 M in hexane) was added dropwise giving a tan slurry.

(d) 37.75 g (0.206 mol) of saccharin was dissolved in 400 ml of dry tetrahydrofuran under nitrogen at −65° C. 85.8 ml (0.206 mol) of n-butyllithium (2.4 M in hexane) was added dropwise until a permanent orange colored endpoint was reached. The mixture was stirred for 1 hour at −65° C. and then used directly in step (e).

(e) The mixture of step (d) was added to the tan slurry of step (c) at −60° C. to −50° C. through a double ended needle. After the addition was completed, the reaction mixture was stirred for 1 hour at −60° C. and gradually warmed to room temperature. The reaction mixture was then poured into 800 ml of water and the pH adjusted to 5-6 with conc. HCl. The orange precipitate which formed was collected to give 13.9 g of the title compound. The filtrate was extracted with ether, dried and evaporated to give 46 g of a dark oil. The oil was washed with hot hexane and then dissolved in hot ethanol (500 ml) and 75 drops of conc. HCl was added. The ethanol was cooled and 7.53 g of orange crystals were collected to give the title compound in a total yield of 21.47 g.

EXAMPLE 4

Preparation of the compound having the formula

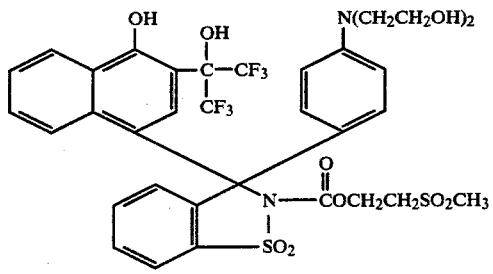

(a) 3-[(3'-α-hydroxy-α-trifluoromethyl-β,β,β-trifluoroethyl)-4'-hydroxy-1'-naphthyl]-3-[4'-N,N-di(β-2"-tetrahydropryanyloxyethyl)-1'-phenyl)benz[d]isothiazole-1,1-dioxide was prepared according to the procedure given in Example 1 above except that 3-[4'-N,N-di(β-2"-tetrahydropyranyloxyethyl)-1'-phenyl]benz[d]isothiazole-1,1-dioxane and 4-bromo-2-(α-hydroxy-α-trifluoromethyl-β,β,β-trifluoroethyl)-1-naphthol were employed in step (a).

(b) The compound prepared in step (a) (2.0 g) was dissolved in approximately 30 ml of pyridine. To this solution was added 20.0 g of Type 3A molecular sieves and 1.13 g of (β-methylsulfonyl)ethylchloroformate and then the reaction mixture was stirred vigorously at room temperature for 3 to 4 hours. TLC on silica gel using 80:20 hexane/acetone showed that a comparatively large amount of starting isothiazole was present. More (β-methylsulfonyl)ethylchloroformate (0.6 g) was added, and the mixture was stirred at room temperature overnight. The following morning only a trace of the starting isothiazole could be detected. The reaction mixture was poured into cold water overlayered with ethyl acetate. The ethyl acetate was decanted, washed with several portions of fresh water, dried over anhydrous sodium sulfate and the solvent removed leaving a dark blue, tacky residue. The residue was dried under vacuum in the presence of phosphorus pentoxide to yield 1.9 g of a dark blue solid.

The tetrahydropyranyl groups were removed by dissolving the blue solid in methanol, made acidic with conc. hydrochloric acid and refluxing for 1 hour. The methanol was removed by evaporation to yield the title compound.

The 3-[4'-N,N-di(β-2''-tetrahydropyranyloxyethyl)-1'-phenyl]benz[d]isothiazole-1,1-dioxide was prepared as follows:

4-Bromo-N,N-di(β-2'-tetrahydropyranyloxyethyl)aniline (10.0 g) was dissolved in 100 ml of tetrahydrofuran. The solution was cooled to −65° C. and 10 ml of n-butyllithium (2.4 M in hexane) was added dropwise under nitrogen at a rate to maintain the temperature below −65° C.

In a separate flask, saccharin (4.28 g) was dissolved in 50 ml of tetrahydrofuran under nitrogen, and the solution was cooled to −65° C. n-Butyllithium (2.4 M in hexane) was added until a peach color persisted (about 9.0 ml).

The latter solution of the N-lithium salt of saccharin was added to the aniline solution by hollow wire over a 10 minute period. (Initially a green color formed which changed to tan.) The reaction mixture was stirred for 1.5 hours and poured into 2 liters of water. The pH was adjusted to 6 with conc. HCl, and the mixture extracted with ether. The ether extract was dried and evaporated and the residue was dissolved in 100 ml of toluene. Two spatula tips of toluene sulfonic acid monohydrate were added, and the solution was refluxed for about 6 hours. The toluene was evaporated and the residue was dissolved in 2 liters of ether. The ether solution was cooled and the crystalline solid was collected to give 4.0 g of the title compound (melting range 100°–101° C.).

Tetrahydropyranylation of p-Br-N,N-di(β-hydroxyethyl)aniline was carried out as follows:

p-Br-N,N-di(β-hydroxyethyl)aniline (20.0 g) was dissolved in 475 ml of dichloromethane containing 60 ml of dihydropyran. To this solution was added 1 ml of conc. HCl, and the reaction solution was stirred for about 5.5 hours. The solution was then washed with water containing enough sodium hydroxide to neutralize any acid present. The dichloromethane was separated, dried over anhydrous sodium sulfate and evaporated under reduced pressure with a steam bath (aspirator) leaving an oil. The oil was heated to 115° C. at 0.1 mm Hg to distill off impurities leaving 33.0 g of the title compound.

EXAMPLE 5

Preparation of the compound having the formula

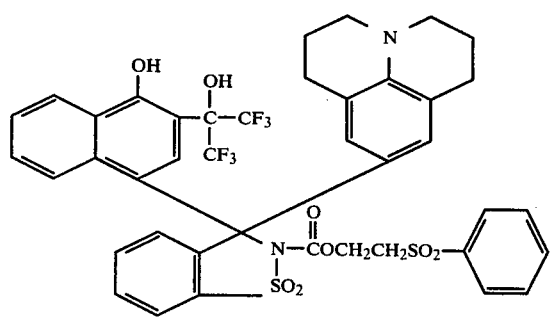

The title compound was prepared according to the procedure given in Example 2 using

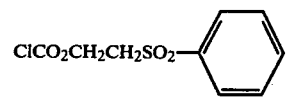

in (b).

The intermediate having the following formula

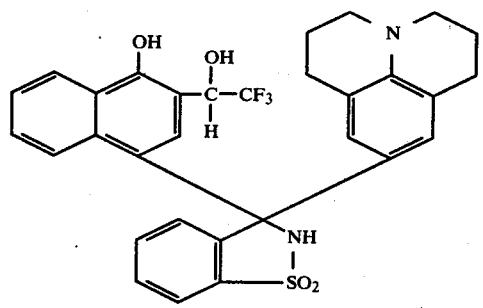

was prepared according to the procedure given in Example 1 above except that 4-bromo-2-(α-hydroxy-β,β,β-trifluoroethyl)-1-naphthol was employed with 3-(9'-julolidinyl)-benz[d]isothiazole-1,1-dioxide in step (a).

The intermediate having the following formula

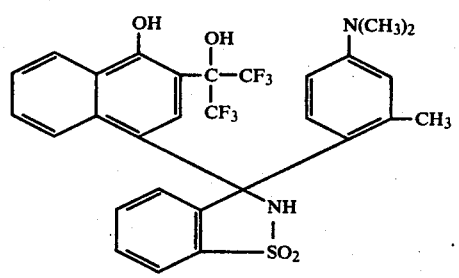

also was prepared according to the procedure given in step (a) of Example 1 above except that 4-bromo-2-(α-hydroxy-α-trifluoromethyl-β,β,β-trifluoromethyl)-1-naphthol was employed with 3-(4'-dimethylamino-2'-methyl-1'-phenyl)-benz[d]isothiazole-1,1-dioxide.

4-Bromo-2-(α-hydroxy-α-trifluoromethyl-β,β,β-trifluoroethyl)-1-naphthol was prepared by adding a suspension of 50 g (0.161 mole) of 2-(α-hydroxy-α-trifluoromethyl)-1-naphthol in 500 ml of CCL$_4$ to a 3-necked, 2-liter flask equipped with a mechanical stirrer. This suspension was stirred while a solution of 8.5 ml (0.161 mole) Br$_2$ in 200 ml CCL$_4$ was added dropwise. Upon completion of the addition, the mixture was stirred for 2 hours, then filtered, and the filtrate evaporated under reduced pressure to leave a tan solid. This solid was dissolved with heating on a steam bath into 300 ml of ligroin (b.p. 90°–110° C.). 10 Grams of norit was added, heating was continued for a further 10 minutes, and then the mixture was filtered through a sintered glass funnel containing a celite pad. Upon cooling and filtration, 50 g of white crystals were collected (melting range 116°–117° C.). The mother liquor was concentrated to one-half the original volume and a second crop of 5 g (melting range 112°–115° C.) was collected to give a total yield of 55 g (88%).

Where it is desired to prepare sulfamnaphthaleins, it will be appreciated that 2,3-dihydro-3-oxo-naptho[1,8-de]-1,2-thiazine-1,1-dioxide or its pseudo-chloride may be substituted for the saccharin reagents used in the foregoing Examples to give the corresponding sulfamnaphthalein intermediates and products. The pseudo-chloride may be prepared from the 3-oxo thiazine by reaction with $PCl_5$.

As noted above, the compounds comprising the light-screening dyes of the present invention are colored and absorb visible radiation below a predetermined alkaline pH, usually pH 10 to 12, and are converted to a product which is colorless, i.e., a non-light-absorbing in the visible range after remaining in contact with base above said predetermined alkaline pH for a predetermined time. For example, the light-screening dyes of the preferred embodiment having a λmax greater than 550 nm initially are cyan and are converted to a blue-violet form in base above a predetermined pH, which violet form decolorizes by undergoing an irreversible cleavage reaction after remaining in contact with said base above said predetermined pH for a predetermined time to yield a colorless product. The colorless product produced by the irreversible cleavage reaction with base is a new compound which possesses a different substituent on the N atom of the sulfam(na)phthalein ring and which is not only different from the colored forms but is non-reversible to the colored forms by changes in pH. Because the subject light-screening dyes are readily and irreversibly discharged, i.e., decolorized, they are particularly useful in photographic systems where permanently bleachable light-screening dyes are necessary or desired.

Typically, the light-screening dyes of the present invention may be employed as antihalation dyes, e.g., in a non-light-sensitive layer positioned intermediate a photosensitive silver halide emulsion layer and the support. Also, they may be employed, e.g., as cyan color correction filter dyes where absorption of red light during exposure is desirable for achieving appropriate color balance and as optical filter agents, e.g., in a preformed titanium dioxide layer to protect a photosensitive layer(s) from post-exposure fogging during processing in the presence of ambient light.

Illustrative film units in which the light-screening dyes of the present invention may be advantageously used as antihalation dyes are described, for example, in commonly assigned copending U.S. Patent Application Ser. No. 383,261 of Edwin H. Land filed July 27, 1973, the specification of which, for convenience, is specifically incorporated herein. These film units comprise, in the order in which incident light passes therethrough, an additive mulicolor screen, a photosensitive silver halide emulsion layer, an antihalation layer in which the selected compound may be disposed, and preferably, an image-receiving layer. As described therein, exposure of the silver halide layer is accmplished through the screen which possesses optical filter elements selectively transmitting predetermined portions of incident radiation, e.g., red, green and blue light, to the underlying photosensitive silver halide layer. Upon photographic processing with an aqueous alkaline processing composition, soluble silver complex is transferred by diffusion and deposited in a superposed image-receiving layer as a function of the degree of exposure of silver halide behind each filter element. The silver image thus formed may then serve to modulate the quantity of light passing through the filter elements in the reverse direction during projection through a transparent support.

In a preferred embodiment, the image-receiving layer is intermediate the photosensitive silver halide emulsion layer and the additive multicolor screen and remains in position as part of an integral film unit prior to, during and after formation of the image. The antihalation dye is disposed in a processing composition permeable layer adjacent to the photosensitive layer on the side opposite the screen and serves to prevent the reflection or back-scattering of incident light which has passed through the photosensitive layer thereby eliminating the exposure of silver halide grains in the photosensitive layer other than those within the intended photoexposure path.

As noted above, the light-screening dyes of the present invention also are useful as color correction filter dyes in photographic film units comprising multilayered, multicolor photosensitive elements employing a blue-, a green-, and a red-sensitive silver halide layer, and particularly in integral negative-positive diffusion transfer film units wherein the image-receiving layer carrying the color transfer image is not separated from the developed photosensitive layers after processing but both components are retained together as a permanent laminate. Included as part of the laminate is a layer of light-reflecting material, preferably titanium dioxide, positioned between the image-carrying layer and the developed photosensitive layer(s). The light-reflecting layer separating the image-carrying and photosensitive components provides a white background for the transfer image and masks the developed photosensitive layer(s). In addition to these layers, the laminate usually includes dimensionally stable outer layers or supports, at least one of which is transparent so that the resulting transfer image may be viewed by reflection against the background provided by the light-reflecting layer.

Illustrative of patents describing such film units are U.S. Pat. No. 2,983,606 issued Mar. 9, 1961 to Howard G. Rogers, U.S. Pat. Nos. 3,415,644, 3,415,645 and 3,415,646 issued Dec. 10, 1968 to Edwin H. Land, U.S. Pat. Nos. 3,594,164 and 3,594,165 issued July 20, 1971 to Howard G. Rogers, and U.S. Pat. No. 3,647,437 issued Mar. 7, 1972 to Edwin H. Land. As noted above, commonly assigned copending U.S. Patent application Ser. No. 537,124 of Edwin H. Land is concerned with multicolor diffusion transfer film units, wherein a layer of a dye, preferably a dye bleachable by the processing composition, is so positioned that photoexposure is effected therethrough, whereby said dye layer is effective as a color correction filter. For convenience, the specification of this application is specifically incorporated herein.

Whether used as antihalation dyes, color correction filter dyes or in other conventional photographic light-screening applications, the compounds of the present invention when disposed in a processing composition-permeable layer are completely and irreversibly decolorized after remaining in contact with an aqueous alkaline processing composition above a predetermined pH for a predetermined time. The preferred compounds have a half-life ($T \frac{1}{2}$) in approximately 1 N NaOH of about 30 seconds or less. As noted above, upon contact with said alkali, the dyes change from their initially colored form to a second colored species substantially instantaneously and then to colorless. By $T \frac{1}{2}$ is meant the time measured for one-half of said second species to decolorize.

The dyes of the present invention may be incorporated into the appropriate layer of the photographic film unit using any of the techniques known in the art. For instance, the selected compound can be dissolved in the appropriate solvent and then dispersed, in the presence of a wetting agent if desired, in a coating solution containing a hydrophilic colloid binder, e.g. gelatin, and the resulting coating solution applied as the desired layer, for example, coated on a transparent support to provide an antihalation layer, or coated over the outermost photosensitive layer of a multilayered, multicolor photosensitive element to provide a color correction filter layer through which photoexposure is made. The concentration of compound in the layer will vary depending upon the product in which the filter layer is to be used and may be readily determined empirically to provide the optical density necessary for the specific use. It will be appreciated that the dyes of the present invention may be used in combination with each other and also may be used in combination with other light-screening dyes previously employed in antihalation, color correction and other filter layers.

FIG. 1 of the accompanying drawing, which illustrates one embodiment of the present invention, is an enlarged cross-sectional view of an integral diffusion transfer film unit comprising a transparent film base or support 1 carrying on one surface, in order, additive multicolor screen 3 comprising a plurality of primary red color filter elements, a plurality of primary green color filter elements and a plurality of blue color filter elements arranged in a geometrically repetitive distribution in side-by-side relationship in substantially a single plane, photoinsensitive layer 5 carrying silver precipitating nuclei, photosensitive layer 7 containing silver halide crystals and antihalation layer 9 containing one or more light-screening dyes of the present invention.

As discussed in aforementioned commonly assigned copending U.S. Patent Application Ser. No. 383,261, the degree of light absorption of the antihalation layer in such film units can vary over a relatively wide range, but usually, the antihalation layer possesses a transmission density range from about 0.4 to 1.4. Preferably, the transmission density is greater than 0.6 so that in the event a plurality of film units is employed in a stacked relationship during photoexposure, the antihalation layer will have sufficient density, i.e., light-absorbing capacity to substantially prevent reflectance as well as prevent exposure of underlying film units.

In determining the appropriate light-absorbing capacity for cyan, magenta and yellow for color correction purposes, "color compensating" filters as conventionally used in front of the camera lens may be employed in the usual manner as a convenient method of approximating the type and quantity of filtration which it would be desirable to provide. A layer containing the appropriate color correction dye(s) in a corresponding density may then be provided as a layer through which photoexposure is to be made.

Multicolor diffusion transfer images may be obtained using a variety of arrangements of the image-receiving layer and the silver halide emulsions. Thus, these layers may be carried by a common support brought into superposition after photoexposure. A particularly advantageous film structure is shown in U.S. Pat. No. 3,415,644 wherein the requisite layers are in superposed relationship prior to and during photoexposure, and these layers are maintained in superposed relationship as a permanent laminate after processing and image formation. Such film units typically contain an outer transparent layer or support through which photoexposure is effected and the final multicolor image viewed, and another outer layer or support carrying at least the photosensitive layers, the latter support being opaque. While these supports or sheet-like elements may simply be held in superposed relationship, e.g., by a binding tape around the edges, in the preferred embodiment these elements are laminated together prior to photoexposure. This prelamination provides a number of benefits, both during manufacture and in photoexposure. Following exposure, the elements are delaminated by the distribution of a fluid processing composition which, upon solidification, bonds the elements together to form the desired permanent laminate. Procedures for forming such prelaminated film units wherein the two elements are temporarily laminated together prior to exposure are described, for example, in U.S. Pat. No. 3,625,231 to Albert J. Bachelder and Frederick J. Binda, and U.S. Pat. No. 3,652,282 to Edwin H. Land, both issued Mar. 28, 1972 and in U.S. Pat. No. 3,793,023 issued to Edwin H. Land on Feb. 19, 1974.

Figure 2:
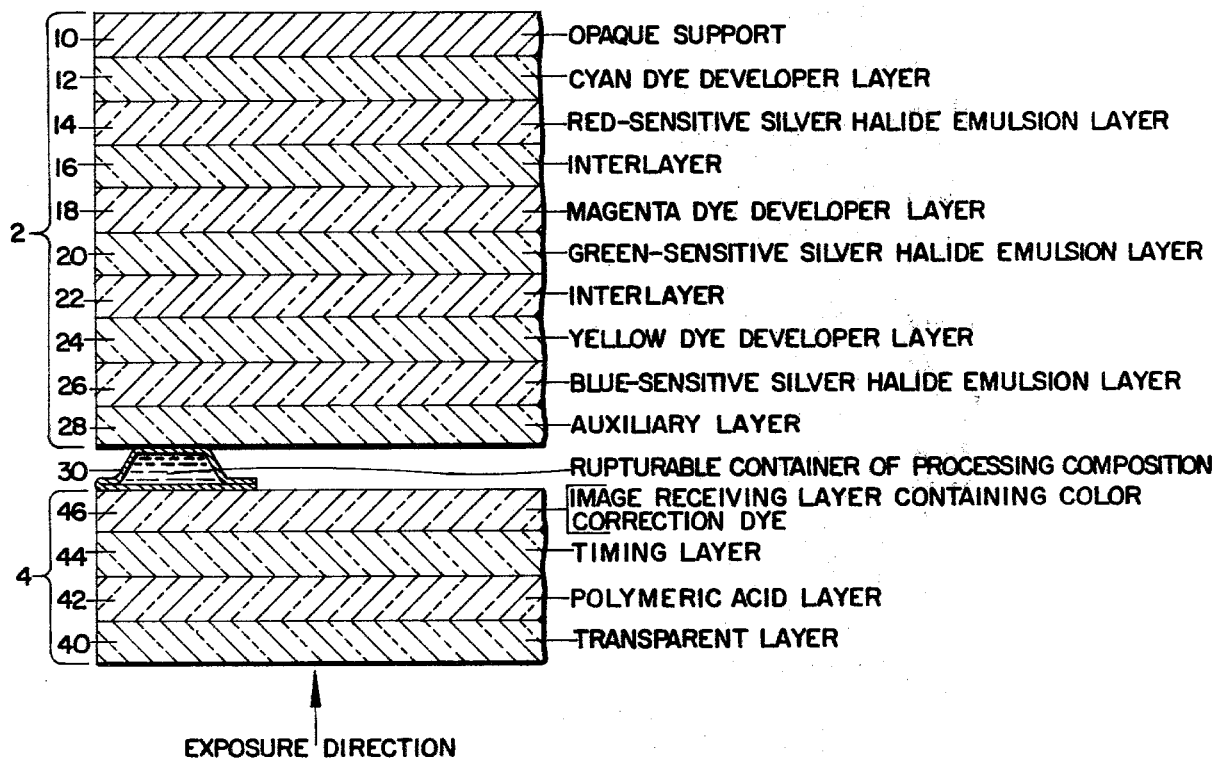
FIG. 2 is a diagrammatic, enlarged cross-sectional view of another diffusion transfer film unit incorporating a light-screening dye of the present invention as a color correction filter dye in the image-receiving layer.

Further description of this embodiment of the present invention may be facilitated by reference to FIG. 2 of the accompanying drawing which illustrates a diffusion transfer film unit adapted to provide integral negative-positive reflection prints and employing dye developers as the image dyes.

FIG. 2 illustrates a diffusion transfer film unit comprising a photosensitive element or component 2, a rupturable container 30, and an image-receiving element or component 4. The photosensitive element 2 comprises an opaque support 10 carrying, in turn, a cyan dye developer layer 12, a red-sensitive silver halide emulsion layer 14, an interlayer 16, a magenta dye developer layer 18, a green-sensitive silver halide emulsion layer 20, an interlayer 22, a yellow dye developer layer 24, a blue-sensitive silver halide emulsion layer 26, and an auxiliary layer 28. The positive or image-receiving element 4 comprises a transparent support 40 carrying, in turn, a polymeric acid layer 42, a timing layer 44 and an image-receiving layer 46 having dispersed therein a bleachable, light-screening dye of this invention as a color correction filter dye. The two elements are held in superposed, registered relationship, e.g., by a binding tape (not shown), so that photoexposure of the silver halide emulsion layers is effected through image-receiving layer 46 containing the bleachable dye. The rupturable container 30 contains a processing composition and is so positioned that, upon rupture the processing composition is distributed between the superposed elements 2 and 4. By including in the processing composition a light-reflecting pigment, preferably titanium dioxide, a light-reflecting layer may be provided against which the transfer image formed in the image-receiving layer 46 may be viewed. The developed photosensitive layers are masked from view by the light-reflecting layer and remain with the receiving layer 46 as part of a permanent laminate. The rupturable container 30 is of the type shown in U.S. Pat. No. 2,543,181 and is positioned adjacent the leading edge of the film unit.

In the processing of the film unit, the film unit is advanced relative to and between a pair of pressure-applying members which apply compressive pressure to the rupturable container 30 to eject its liquid contents between the photosensitive and image-receiving components 2 and 4 and then distribute the mass of liquid between the sheets toward the trailing ends thereof to form a layer of substantially uniform, predetermined thickness at least co-extensive with the image area. In order to insure sufficient processing liquid to form a layer of the required area and thickness between the sheets, excess processing liquid may be provided in container 30 and trapping means (not shown) provided for collecting and retaining excess processing liquid overrun. Details of the various layers of this and of the film unit of FIG. 1 may be found in the herein cited patents and applications and need not be recited here.

Processing of film units of the type described in FIG. 2 is initiated by distributing the processing composition between predetermined layers of the film unit. In exposed and developed areas, the dye developer will be immobilized as a function of development. In unexposed and undeveloped areas, the dye developer is unreacted and diffusible, and this provides an imagewise distribution of unoxidized dye developer, diffusible in the processing composition, as a function of the point-to-point degree of exposure of the silver halide layer. The desired transfer image is obtained by the diffusion transfer to the image-receiving layer of at least part of this imagewise distribution of unoxidized dye developer. In the illustrated embodiment, the pH of the photographic system is controlled and reduced by the neutralization of alkali after a predetermined interval, in accordance with the teachings of the above noted U.S. Pat. No. 3,615,644, to reduce the alkalinity to a pH at which the unoxidized dye developer is substantially insoluble and non-diffusible. As will be readily recognized, the details of such processes form no part of the present invention but are well known; the previously noted U.S. patents may be referred to for more specific discussion of such processes.

Multicolor images may be obtained by providing the requisite number of differentially exposable silver halide emulsions, and said silver halide emulsions are most commonly provided as individual layers coated in superposed relationship. Film units intended to provide multicolor images comprise two or more selectively sensitized silver halide layers each having associated therewith an appropriate image dye-providing material providing an image dye having spectral absorption characteristics substantially complementary to the light by which the associated silver halide is exposed. The most commonly employed negative components for forming multicolor images are the "tripack" structure and contain blue-, green-, and red-sensitive silver halide layers each having associated therewith in the same or in a contiguous layer a yellow, a magenta and a cyan image dye-providing material respectively. Interlayers or spacer layers may, if desired, be provided between the respective silver halide layers and associated image dye-providing materials or between other layers. Integral multicolor photosensitive elements of this general type are disclosed in U.S. Pat. No. 3,345,163 issued Oct. 3, 1967 to Edwin H. Land and Howard G. Rogers as well as in the previously noted U.S. patents, e.g., in FIG. 9 of the aforementioned U.S. Pat. No. 2,983,606.

A number of modifications to the structures described in connection with FIG. 2 will readily suggest themselves to one skilled in the art. Thus, for example, the multicolor multilayer negative may be replaced by a screen-type negative as illustrated in U.S. Pat. No. 2,968,554 issued Jan. 17, 1961 to Edwin H. Land and in the aforementioned U.S. Pat. No. 2,983,606 particularly with respect to FIG. 3 thereof.

The image dye-providing materials which may be employed in such processes generally may be characterized as either (1) initially soluble or diffusible in the processing composition but are selectively rendered non-diffusible in an imagewise pattern as a function of development; or (2) initially insoluble or non-diffusible in the processing composition but which are selectively rendered diffusible or provide a diffusible product in an imagewise pattern as a function of development. These materials may be complete dyes or dye intermediates, e.g., color couplers. The requisite differential in mobility or solubility may, for example, be obtained by a chemical action such as a redox reaction or a coupling reaction.

As examples of initially soluble or diffusible materials and their application in color diffusion transfer, mention may be made of those disclosed, for example, in U.S. Pat. Nos. 2,774,668; 2,968,554; 2,983,606; 3,087,817; 3,185,567; 3,230,082; 3,345,163; and 3,443,943. As examples of initially non-diffusible materials and their use in color transfer systems, mention may be made of the materials and systems disclosed in U.S. Pat. Nos. 3,185,567; 3,719,489; 3,443,939; 3,443,940; 3,227,550; and 3,227,552. Many types of image dye-providing substances and film units useful therewith also are discussed in the aforementioned U.S. Pat. No. 3,647,437 to which reference may be made.

It is also to be understood that "direct positive" silver halide emulsions may also be used, depending upon the particular image dye-providing substances employed and whether a positive or negative color transfer image is desired.

A preferred opacification system to be contained in the processing composition to effect processing outside of a camera is that described in the above-mentioned U.S. Pat. No. 3,647,437, and comprises a dispersion of an inorganic light-reflecting pigment which also contains at least one light-absorbing agent, i.e., optical filter agent, at a pH above the pKa of the optical filter agent in a concentration effective when the processing composition is applied, to provide a layer exhibiting optical transmission density > than about 6.0 density units with respect to incident radiation actinic to the photosensitive silver halide and optical deflection density < than about 1.0 density units with respect to incident visible radiation.

In lieu of having the light-reflecting pigment in the processing composition, the light-reflecting pigment used to mask the photosensitive strata and to provide the background for viewing the color transfer image formed in the receiving layer may be present initially in whole or in part as a preformed layer in the film unit. As an example of such a preformed layer, mention may be made of that disclosed in U.S. Pat. No. 3,615,421 issued Oct. 26, 1971 and in U.S. Pat. No. 3,620,724 issued Nov. 16, 1971, both in the name of Edwin H. Land. The reflecting agent may be generated in situ as is disclosed in U.S. Pat. Nos. 3,647,434 and 3,647,435, both issued Mar. 7, 1972 to Edwin H. Land.

The dye developers (or other image dye-providing substances) are preferably selected for their ability to provide colors that are useful in carrying out subtractive color photography, that is, the previously mentioned cyan, magenta and yellow. They may be incorporated in the respective silver halide emulsion or, in the preferred embodiment, in a separate layer behind the respective silver halide emulsion. Thus, a dye developer may, for example, be in a coating or layer behind the respective silver halide emulsion and such a layer of dye developer may be applied by use of a coating solution containing the respective dye developer distributed, in a concentration calculated to give the desired coverage of dye developer per unit area, in a film-forming natural, or synthetic, polymer, for example, gelatin, polyvinyl alcohol, and the like, adapted to be permeated by the processing composition.

Dye developers, as noted above, are compounds which contain the chromophoric system of a dye and also a silver halide developing function. By "a silver halide developing function" is meant a grouping adapted to develop exposed silver halide. A preferred silver halide development function is a hydroquinonyl group. Other suitable developing functions include ortho-dihydroxyphenyl and ortho- and paraamino substituted hydroxyphenyl groups. In general, the development function includes a benzenoid developing function, that is, an aromatic developing group which forms quinonoid or quinone substances when oxidized.

The image-receiving layer may comprise one of the materials known in the art, such as polyvinyl alcohol, gelatin, etc. It may contain agents adapted to mordant or otherwise fix the transferred image dye(s). Preferred materials comprise polyvinyl alcohol or gelatin containing a dye mordant such as poly-4-vinylpyridine, as disclosed in U.S. Pat. No. 3,148,061 and graft copolymers containing 4-vinylpyridine as disclosed in U.S. Pat. No. 3,756,814.

In the various color diffusion transfer systems which have previously been described and which employ an aqueous alkaline processing fluid, it is well known to employ an acid-reacting reagent in a layer of the film unit to lower the environmental pH following substantial dye transfer in order to increase the image stability and/or to adjust the pH from the first pH at which the image dyes are diffusible to a second (lower) pH at which they are not. For example, the previously mentioned U.S. Pat. No. 3,415,644 discloses systems wherein the desired pH reduction may be effected by providing a polymeric acid layer adjacent the dyeable stratum. These polymeric acids may be polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups. Alternatively, the acid-reacting reagent may be in a layer adjacent to the silver halide most distant from the image-receiving layer, as disclosed in U.S. Pat. No. 3,573,043 issued Mar. 30, 1971 to Edwin H. Land. Another system for providing an acid-reacting reagent is disclosed in U.S. Pat. No. 3,576,625 issued Apr. 27, 1971 to Edwin H. Land.

An inert interlayer or spacer layer may be and is preferably disposed between the polymeric acid layer and the dyeable stratum in order to control or "time" the pH reduction so that it is not premature and interferes with the development process. Suitable spacer or "timing" layers for this purpose are described with particularity in U.S. Pat. Nos. 3,362,819; 3,419,389; 3,421,893; 3,455,686; and 3,575,701.

While the acid layer and associated spacer layer are preferably contained in the positive component employed in systems wherein the dyeable stratum and photosensitive strata are contained on separate supports, e.g., between the support for the receiving element and the dyeable stratum; or associated with the dyeable stratum in those integral film units, e.g., on the side of the dyeable stratum opposed from the negative components, they may, if desired, be associated with the photosensitive strata, as is disclosed, for example, in U.S. Pat. Nos. 3,362,821 and 3,573,043. In film units such as those described in the aforementioned U.S. Pat. Nos. 3,594,164 and 3,594,165, they also may be contained on the spreader sheet employed to facilitate application of the processing fluid.

As is now well known and illustrated, for example, in the previously cited patents, the liquid processing composition referred to for effecting multicolor diffusion transfer processes comprises at least an aqueous solution of an alkaline material, for example sodium hydroxide, potassium hydroxide, and the like, and preferably possessing a pH in excess of 12, and most preferably includes a viscosity-increasing compound constituting a film-forming material of the type which, when the composition is spread and dried, forms a relatively firm and relatively stable film. The preferred film-forming materials comprise high molecular weight polymers such as polymeric, water-soluble ethers which are inert to an alkaline solution such as, for example, a hydroxyethyl cellulose or sodium carboxymethyl cellulose. Other film-forming materials or thickening agents whose ability to increase viscosity is substantially unaffected if left in solution for a long period of time also are capable of utilization. The film-forming material is preferably contained in the processing composition in such suitable quantities as to impart to the composition a viscosity in excess of 100 cps, at a temperature of approximately 24° C. and preferably in the order of 100,000 cps to 200,000 cps at that temperature.

In particularly useful embodiments, the transparent polymeric support contains a small quantity of a pigment, e.g., carbon black, to prevent fog formation due to light-piping by internal reflection within the transparent support, and subsequent exiting from the support surface carrying the photographic layers, of actinic light incident upon an edge thereof; such elements are described in Belgian Pat. No. 777,407. The transparent support advantageously may include an ultraviolet light absorber.

For purposes of illustrating the invention, a multicolor photosensitive element using, as the cyan, magenta and yellow dye developers

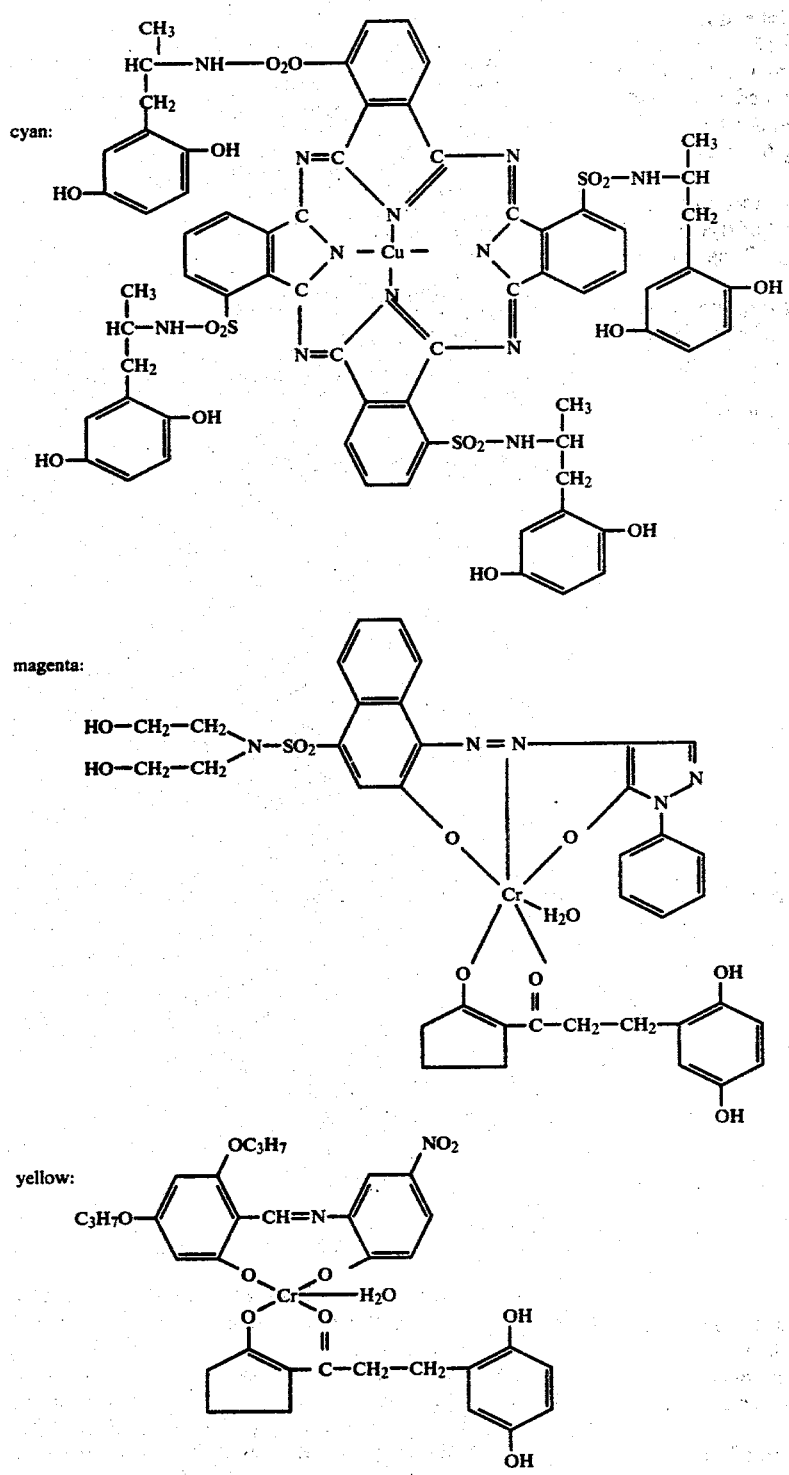

was prepared by coating a gelatin-subcoated 4 mil opaque polyethylene terephthalate film base with the following layers:

1. a layer of cyan dye developer dispersed in gelatin and coated at a coverage of 69 mgs./ft.$^2$ of dye and 138 mgs./ft.$^2$ of gelatin, plus 4′-methylphenyl hydroquinone coated at a coverage of 6.3 mgs./ft.$^2$ and 2-phenylbenzimidazole coated at a coverage of 25.1 mgs./ft.$^2$;

2. a red-sensitive gelatino silver iodobromide emulsion coated at a coverage of 120 mgs./ft.$^2$ of silver halide;

3. a layer of 60-30-4-6 tetrapolymer of butylacrylate, diacetone acrylamide, styrene and methacrylic acid and polyacrylamide coated at a coverage of 232.8 mgs./ft.$^2$ of the copolymer and 7.2 mgs./ft.$^2$ of polyacrylamide;

4. a layer of magenta dye developer dispersed in gelatin and coated at a coverage of 60 mgs./ft.$^2$ of dye and 42 mgs./ft.² of gelatin; and about 21 mgs./ft.² of 2-phenylbenzimidazole;

5. a green-sensitive gelatino silver iodobromide emulsion at a coverage of about 74 mgs./ft.² of silver halide;

6. a layer containing the tetrapolymer referred to 5 above in layer 3 plus polyacrylamide coated at a coverage of 126.9 mgs./ft.² of tetrapolymer and 8.1 mgs./ft.² of polyacrylamide; and also containing 6.6 mgs./ft.² of succindialdehyde;

7. a layer of yellow dye developer dispersed in gelatin and coated at a coverage of 90 mgs./ft.² of dye and 42 mgs./ft.² of gelatin; and also containing 19 mgs./ft.² of 2-phenylbenzimidazole;

8. a blue-sensitive gelatino silver iodobromide emulsion coated at a coverage of 119 mgs./ft.² of silver and 62 mgs./ft.² of gelatin; and also containing 19 mgs./ft.² of 4'-methylphenylhydroquinone; and 9. a layer of gelatin coated at a coverage of 45 mgs./ft.² of gelatin and also containing carbon black coated at a coverage of 4 mgs./ft.²

The aqueous alkaline processing composition comprised the following in % by weight.

| Water | 49.28 |
| --- | --- |
| Potassium hydroxide | 5.39 |
| Carboxymethyl hydroxyethyl cellulose | 1.79 |
| Benzotriazole | 0.77 |
| 4-aminopyrazolo-3,4-D-pyrimidine | 0.20 |
| 6-methyluracil | 0.21 |
| N-2-hydroxyethyl-N,N',N'-triscarboxymethyl-ethylene diamine | 0.81 |
| bis(2-aminoethyl)sulfide | 0.02 |
| Polyethylene glycol (mol. wt. 6000) | 0.50 |
| Titanium dioxide | 38.10 |
| Colloidal silica aqueous dispersion (30% SiO₂) | 1.68 |
| N-phenethyl-α-picolinium bromide | 1.25 |

To 100 gms. of the above composition was added 1.35 gms. of the pH-sensitive dye of the formula

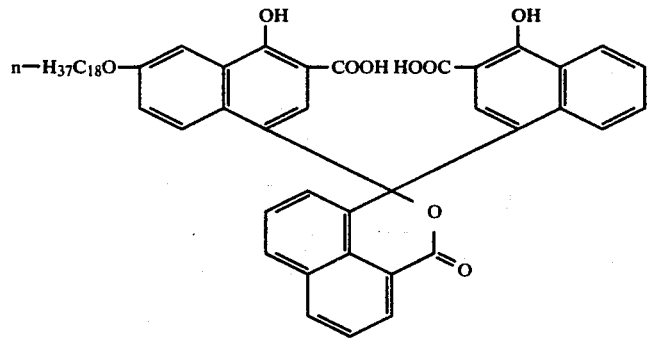

A transparent 4 mil polyethylene terephthalate film base was coated, in succession, with the following layers to form an image-receiving component:

1. as a polymeric acid layer, the partial butyl ester of polyethylene/maleic anhydride copolymer at a coverage of about 2,500 mgs./ft.²;

2. a timing layer containing a 14:1 ratio of a 60-30-4-6 tetrapolymer of butylacrylate, diacetone acrylamide, styrene and methacrylic acid and polyvinyl alcohol at a coverage of 500 mgs./ft.²; and 3. a blend of 3 parts by weight of a 2:1 mixture, by weight, of polyvinyl alcohol and poly-4-vinylpyridine and 1 part by weight of a graft copolymer of 4-vinylpyridine and vinylbenzyltrimethylammoniumchloride grafted on hydroxyethyl cellulose in a weight ratio of 2.2/1/2.2, respectively, coated at a coverage of 300 mgs./ft.² to provide an image-receiving layer.

and 0.30 gms. of the pH-sensitive dye of the formula

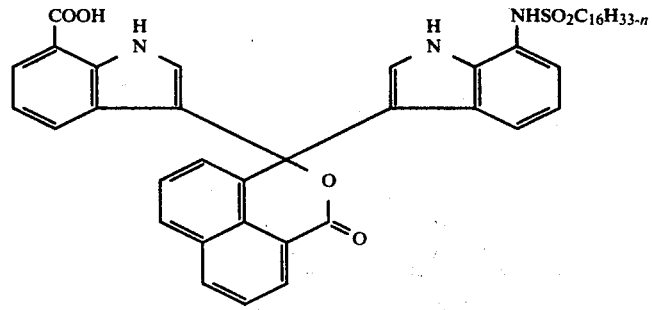

The photosensitive element was exposed to a multicolor stepwedge, the image-receiving element superposed on the exposed photosensitive element, and a rupturable container of the processing composition attached. This assembly was passed between a pair of pressure rolls so that a layer approximately 0.003" thick of the processing composition was distributed between the gelatin overcoat layer 9 of the photosensitive element and the image-receiving layer 3 of the image-receiving element. The blue, green and red D log E curves of the resulting multicolor transfer image (control image) were prepared.

A test multicolor transfer image was prepared in the same manner described above using an identical processing composition and identical photosensitive and image-receiving elements except that the compound prepared in Example 2 above was incorporated in the image-receiving layer 3 at a coverage of 6 mgs./ft.$^2$ The blue, green and red D log E curves of the test image were prepared, and the reflection density for the blue, green and red curves was measured at the 0.75 exposure intercept of the neutral density column for both the control and test multicolor transfer images. The density measurements obtained are set forth in the following Table.

TABLE

| Image | Red | Green | Blue |
| --- | --- | --- | --- |
| Control | 1.63 | 1.58 | 1.57 |
| Test | 1.48 | 1.55 | 1.54 |

It will be appreciated from reference to the Table that the subject dye was effective in absorbing red light. In addition, it was observed that decolorization of the filter dye in the test image occurred in less than 30 seconds.

Also, it will be appreciated that in utilizing the subject dyes to correct color balance, for example, in multicolor diffusion transfer photographic film units that a photosensitive element may be exposed to a suitable multicolor step-wedge and diffusion transfer processed with a given processing composition and image-receiving element. The blue, green and red D log E curves of the resulting multicolor transfer image (sample image) are then prepared. Examination of these D log E curves will indicate to one skilled in color photographic sensitometry the manner and extent to which the individual D log E curves depart from the desired curve shape. From this examination, one may determine by routine analysis and experimentation how much filtration would be required of what wavelength range or ranges to obtain a more desirable color balance. The photosensitive element of another film unit, having the identical photosensitive element, image-receiving element and processing composition as used in obtaining the sample image, is then given the same exposure through a conventional color correction filter(s) of the color and density estimated to be necessary to provide the desired changes in the D log E curves of the sample image. The blue, green and red D log E curves of the resulting test multicolor transfer image are then prepared and compared with the sample. While more than one "test" may be required to determine the color filtration most effective to give the desired D log E curve shape changes, such tests may be performed rapidly and easily. When the appropriate color filtration has been determined, a layer containing a color correction dye or dyes absorbing light in appropriate wavelength range(s) is coated on a transparent support at a coverage calculated to provide the requisite density. This "test" color correction dye layer is placed in the exposure path and the previous exposure test repeated. Analysis of the D log E curves of the resulting multicolor transfer image will indicate what changes, if any, should be made in the spectral absorption range and density prior to incorporating a corresponding color correction dye layer into the diffusion transfer film unit.

The light-screening dyes of the preferred embodiment of this invention are particularly useful for adjusting the red characteristic curve, i.e., D log E curve. Indeed, the compounds of Examples 1 to 5 and the

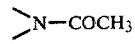

derivatives of the two intermediates prepared above have a λmax greater than about 575 nm in addition to an epsilon of at least 4000 as measured in trifluoroethanol.

It will be recognized that effecting photoexposure through a layer containing the subject dye(s) is effective to "filter", i.e., decrease the exposure given to the silver halide layer(s) exposable by light absorbed by said color correction dye(s) and that one or more dyes of the present invention may be used in conjunction with other filter dyes for effecting changes in one, two or all three of the individual red, green and blue H and D curves to achieve the desired color balance. Though the subject dyes find particular utility in diffusion transfer and other photographic film units where it is desired to bleach the dye(s) during processing subsequent to photoexposure through the dye layer(s), the subject dyes also may be employed in diffusion transfer and other film units where the dye is so positioned as not to contribute dye density to the transfer or final image. Where the filter dye layer through which photoexposure has been made is not part of the transfer image, or where the final image is masked from view as in certain integral negative-positive reflection print structures, the filter dye should be non-diffusible to the image-receiving layer containing the transfer image. The requisite non-diffusion character may be provided by the use of a suitable mordant, by the use of long chain "ballast" or "anchor" substituents and/or other art known techniques.

As noted in the above example, in integral diffusion transfer film units, the color correction dye(s) may be incorporated in the image-receiving layer. The choice of location of the color correction dye(s) will depend in large part upon what stage of the manufacturing process the determination is made to incorporate such a color correction dye. As will be readily apparent, provision of the color correction dye(s) in a separate layer has the advantage of permitting modification after the components have fully "matured" and also permits different modification of portions of the same lot of the positive component.

The supports for the various layers may be any of the types known in the art to be useful. In the preferred embodiments wherein an integral negative-positive reflection print is obtained, the supports should be dimensionally stable and may be polyethylene terephthalate or other polymeric film base, as disclosed in the cross-referred patents.

It will be recognized that the transfer image formed following exposure and processing of film units of the type illustrated in FIG. 2 will be a geometrically reversed image of the subject. Accordingly, to provide geometrically non-reversed transfer images, exposure of such film units should be accomplished through an image reversing optical system, such as in a camera possessing an image reversing optical system utilizing mirror optics, e.g., as described in U.S. Pat. No. 3,447,437 issued June 3, 1969 to Douglas B. Tiffany.

Where the expression "positive image" has been used, this expression should not be interpreted in a restrictive sense since it is used primarily for purposes of illustration, in that it defines the image produced on the image-carrying layer as being reversed, in the positive-negative sense, with respect to the image in the photosensitive emulsion layers. As an example of an alternative meaning for "positive image", assume that the photosensitive element is exposed to actinic light through a negative transparency. In this case, the latent image in the photosensitive emulsion layers will be positive and the dye image produced on the image-carrying layer will be negative. The expression "positive image" is intended to cover such an image produced on the image-carrying layer, as well as transfer images obtained by use of direct positive silver halide emulsions to provide a "positive" image of the photographed subject.

While the usefulness of the subject light-screening dyes has been illustrated as applied to integral diffusion transfer film units where the transfer image is retained with the developed photosensitive element as part of a permanent laminate, it will be understood that the light-screening dyes of this invention also may be used to provide antihalo, color correction or other light filtering layer(s) in diffusion transfer film units where the transfer image, either in silver or in dye, is separated from the developed photosensitive layer(s) subsequent to processing. Though the image dye-providing materials are preferably dye developers, it will be appreciated that other types of image dyes and dye intermediates may be employed to provide the dye transfer image.

Besides their usefulness in diffusion transfer photographic products and processes, the light-screening dyes of the present invention also may be used in filter layers of conventional photographic materials, for example, in antihalation or color correction layers in conventional negatives, and may be disposed in the appropriate layer(s) in an amount sufficient to provide the desired filtering effect. The selection and incorporation of the light-screening dye for the desired filtering effect may be accomplished in a known manner using conventional techniques and is well within the skill of the art. For example, for color correction purposes, the dye(s) selected may absorb light within a specific wavelength range, e.g., blue, green or red light, or within a combination of several wavelength ranges and will be disposed in a layer through which photoexposure is made. Indeed, it may be desirable in a given instance to filter light of two different wavelength ranges in a ratio such that one silver halide emulsion receives more exposure filtration than does another. As in the diffusion transfer film units, the dye(s) selected for color correction are advantageously applied after the photosensitive element has aged to "maturity", i.e., the sensitometry of the photosensitive element as manufactured is no longer changing significantly with time. Where the subject dyes are employed for antihalation purposes, they may be incorporated, for example, in a layer on one or both sides of a support carrying the photosensitive layer(s) and where they are employed as optical filter agents, they will be so positioned as to prevent post-exposure fogging during processing in ambient light without, of course, interfering with imagewise exposure of the photosensitive layer(s) or with viewing of the final image.

Since certain changes may be made in the hereinafter defined subject matter without departing from the scope of the invention herein involved, it is intended that all matter contained in the above description and examples be interpreted as illustrative and not in a limiting sense.

What is claimed is:

1. A photographic product comprising a plurality of layers including a support and at least one photosensitive silver halide emulsion layer carried on said support, at least one of said layers containing a light-screening dye of the formula

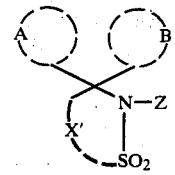

wherein A is a 4'-hydroxy-1'-naphthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol.

2. A photographic product as defined in claim 1 wherein said light-screening dye is disposed in a processing composition permeable layer on the same side of said support as said silver halide emulsion layer(s).

3. A photographic product as defined in claim 2 which comprises, in order, said support, said photosensitive silver halide emulsion layer and said layer containing said light-screening dye.

4. A photographic product as defined in claim 3 which includes a silver-precipitating layer so positioned as to receive a silver diffusion transfer image upon application of an aqueous alkaline processing composition to provide a silver halide developing agent and a silver halide solvent.

5. A photographic product as defined in claim 4 which comprises, in order, said support, an additive multicolor screen, said silver-precipitating layer, said photosensitive silver halide emulsion layer and said layer of said light-screening dye, said support being transparent.

6. A photographic product as defined in claim 2 wherein said support is transparent and said light-screening dye is disposed in a layer between said support and said silver halide emulsion layer(s).

7. A photographic product as defined in claim 6 which additionally includes a layer of said light-screening dye coated over the photosensitive silver halide emulsion layer outermost from said support on the surface opposite said support.

8. A photographic product as defined in claim 2 wherein said silver halide emulsion layers are a red-sensitive silver halide emulsion, a green-sensitive silver halide emulsion and a blue-sensitive silver halide emulsion, each said emulsion layer having an image dye-providing substance associated therewith.

9. A photographic product as defined in claim 1 wherein said light-screening dye is a compound of the formula

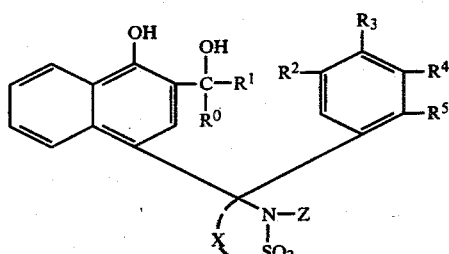

wherein $R^0$ is perhalomethyl selected from trifluoromethyl, difluoromethyl, difluorochloromethyl, dichlorofluoromethyl, dichloromethyl and trichloromethyl; $R^1$ is selected from hydrogen and perhalomethyl having the same meaning given above; $R^2$ and $R^4$ each are selected from hydrogen, alkyl, alkoxy, chloro and fluoro; $R^5$ is hydrogen, hydroxy, alkyl or alkoxy; $R^3$ is pyrrolidino, -N,N-(dialkyl)amino, -N,N-(w-$R^6$-alkyl)$_2$amino wherein $R^6$ is halo or hydroxy; $R^2$, $R^3$ and $R^4$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and Z is

wherein Y is an electron-withdrawing group.

10. A photographic product for forming a multicolor diffusion transfer image, said product comprising a first sheet-like element comprising a first support carrying a red-sensitive silver halide emulsion layer, a green-sensitive silver halide emulsion layer, and a blue-sensitive silver halide emulsion layer, said silver halide emulsion layers having associated therewith, respectively, a cyan image dye-providing material, a magenta image dye-providing material and a yellow image dye-providing material; a second sheet-like element comprising a second support; said first and second sheet-like elements being in superposed relationship, or adapted to be brought into superposed relationship, with said supports being outermost; at least one of said supports being transparent to permit photoexposure of said silver halide emulsions therethrough; a rupturable container releasably holding an aqueous alkaline processing composition, said rupturable container being so positioned as to be capable of discharging said processing composition between a pair of predetermined layers carried by said supports; an image-receiving layer carried by one of said supports; and a light-screening dye being disposed in a processing composition permeable layer carried by one of said supports, said light-screening dye being a compound of the formula

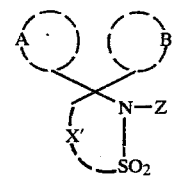

wherein A is a 4'-hydroxy-1'-naphthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol.

11. A photographic product as defined in claim 10 wherein said light-screening dye is so positioned that photoexposure of said silver halide emulsion layers is effected therethrough.

12. A photographic product as defined in claim 11 wherein said second support is transparent and said image-receiving layer and said light-screening dye are carried by said transparent second support of said second sheet-like element.

13. A photographic product as defined in claim 12 wherein said light-screening dye is disposed in said image-receiving layer.

14. A photographic product as defined in claim 12 wherein said first support is opaque.

15. A photographic product as defined in claim 11 wherein said first and second supports are transparent.

16. A photographic product as defined in claim 10 wherein said product includes means providing a layer of a white pigment between said image-receiving layer and said silver halide emulsions.

17. A photographic product as defined in claim 16 wherein said means providing a layer of a white pigment comprises including a pigment dispersed in said processing composition.

18. A photographic product as defined in claim 16 wherein said means providing a layer of a white pigment comprises a preformed layer of a white pigment.

19. A photographic product as defined in claim 18 wherein said light-screening dye is disposed in said preformed layer of a white pigment.

20. A photographic product as defined in claim 10 wherein each said image dye-providing materials is an image dye-providing material selected from image dyes and image dye intermediates.

21. A photographic product as defined in claim 20 wherein each said image dye-providing material is a dye.

22. A photographic product as defined in claim 21 wherein each said dye is a dye developer.

23. A photographic product as defined in claim 10 wherein said first and second sheet-like elements are in superposed relationship.

24. A photographic product as defined in claim 10 wherein said second sheet-like element is adapted to be superposed with said first sheet-like element.

25. A photographic product as defined in claim 10 wherein said light-screening dye is a compound of the formula

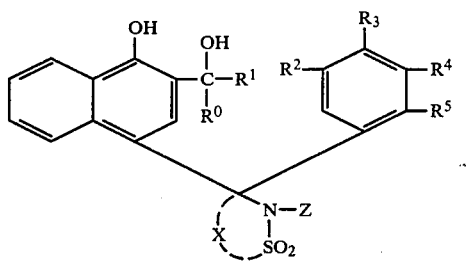

wherein $R^0$ is perhalomethyl selected from trifluoromethyl, difluoromethyl, difluorochloromethyl, dichlorofluoromethyl, dichloromethyl and trichloromethyl; $R^1$ is selected from hydrogen and perhalomethyl having the same meaning given above; $R^2$ and $R^4$ each are selected from hydrogen, alkyl, alkoxy, chloro and fluoro; $R^5$ is hydrogen, hydroxy, alkyl or alkoxy; $R^3$ is pyrrolidino, -N,N-(dialkyl)amino, -N,N-(w-$R^6$-alkyl)$_2$amino wherein $R^6$ is halo or hydroxy; $R^2$, $R^3$ and $R^4$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and Z is

wherein Y is an electron-withdrawing group.

26. A photographic process which comprises the steps of exposing a photosensitive film unit comprising a plurality of layers including at least one photosensitive silver halide emulsion layer carried on a support, at least one of said layers containing a colored light-screening dye of the formula

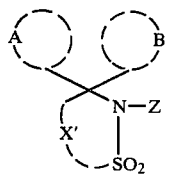

wherein A is a 4'-hydroxy-1'-naphthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol and contacting said photosensitive silver halide emulsion layer(s) with an aqueous alkaline processing composition having an alkaline pH above said predetermined pH to effect development.

27. A photographic process as defined in claim 26 wherein said light-screening dye is disposed in a processing composition permeable layer on the same side of said support as said silver halide emulsion layer and the pH of said processing composition in contact with said light-screening dye is maintained above said predetermined pH for a time sufficient to effect cleavage of said Z moiety whereby said colored light-screening dye is converted to a colorless compound.

28. A photographic process as defined in claim 27 wherein said support is transparent and said light-screening dye is disposed in a layer between said support and said silver halide emulsion layer(s).

29. A photographic process as defined in claim 28 wherein said film unit includes a layer of said light-screening dye coated over the silver halide emulsion layer outermost from said support on the surface opposite said support.

30. A photographic process as defined in claim 27 wherein said silver halide emulsion layers are a red-sensitive silver halide layer, a green-sensitive silver halide layer and a blue-sensitive silver halide layer, each said emulsion layer having an image dye-providing material associated therewith.

31. A photographic process as defined in claim 27 including the step of separating said processing composition from contact with said film unit subsequent to development and irreversible cleavage of said Z moiety.

32. A photographic process as defined in claim 26 which comprises, in combination, the steps of:
(a) exposing said photosensitive film unit comprising a plurality of layers including a support carrying at least one photosensitive silver halide emulsion layer having associated therewith an image-providing material, an image-receiving layer adapted to receive solubilized image-providing material diffusing thereto, at least one of said layers on the same side of said support as said silver halide layer(s) containing a colored light-screening dye of the formula

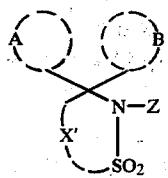

wherein A is a 4'-hydroxy-1'-naphthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol;
(b) contacting said silver halide layer(s) and said light-screening dye with a processing composition having an alkaline pH above said predetermined pH;
(c) effecting thereby development of said silver halide layer(s);
(d) maintaining the pH of said processing composition in contact with said light-screening dye above said predetermined alkaline pH for a time sufficient to effect irreversible cleavage of said Z moiety whereby said colored light-screening dye is converted to a colorless compound;
(e) forming as a result of said development, an imagewise distribution of diffusible image-providing material; and
(f) transferring, by diffusion, at least a portion of said imagewise distribution of diffusible image-providing material to said layer adapted to receive said material to provide a transfer image thereto.

33. A photographic process as defined in claim 32 which includes the step of maintaining said film unit intact subsequent to said processing.

34. A photographic process as defined in claim 33 wherein said processing composition includes a silver halide solvent and said transfer image is an image in silver.

35. A photographic process as defined in claim 34 wherein said photosensitive film unit comprises, in order, a transparent support, an additive multicolor screen, an image-receiving layer comprising a silver-precipitating layer, a photosensitive silver halide emulsion layer and a layer of said light-screening dye.

36. A photographic process as defined in claim 26 wherein said light-screening dye is a compound of the formula

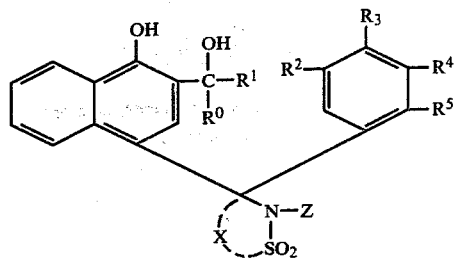

wherein $R^0$ is perhalomethyl selected from trifluoromethyl, difluoromethyl, difluorochloromethyl, dichlorofluoromethyl, dichloromethyl and trichloromethyl; $R^1$ is selected from hydrogen and perhalomethyl having the same meaning given above; $R^2$ and $R^4$ each are selected from hydrogen, alkyl, alkoxy, chloro and fluoro; $R^5$ is hydrogen, hydroxy, alkyl or alkoxy; $R^3$ is pyrrolidino, -N,N-(dialkyl)amino, -N,N-(w-$R^6$-alkyl)$_2$amino wherein $R^6$ is halo or hydroxy; $R^2$, $R^3$ and $R^4$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and Z is

wherein Y is an electron-withdrawing group.

37. A photographic process for forming a multicolor diffusion transfer image which comprises the steps of:
(a) exposing a photosensitive film unit which includes, in combination, a first sheet-like element comprising a first support carrying a red-sensitive silver halide emulsion layer, a green-sensitive silver halide emulsion layer, and a blue-sensitive silver halide emulsion layer, said silver halide emulsion layers having associated therewith, respectively, a cyan image dye-providing material, a magenta image dye-providing material and a yellow image dye-providing material; a second sheet-like element comprising a second support; said first and second sheet-like elements being in superposed relationship, or adapted to be brought into superposed relationship, with said supports being outermost; at least one of said supports being transparent to permit photoexposure of said silver halide emulsions therethrough; a rupturable container releasably holding an aqueous alkaline processing composition, said rupturable container being so positioned as to be capable of discharging said processing composition between a pair of predetermined layers carried by said supports; an image-receiving layer carried by one of said supports; and a colored light-screening dye disposed in a processing composition permeable layer carried by one of said supports, said light-screening dye being a compound of the formula

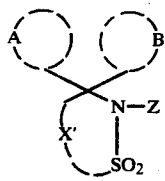

wherein A is a 4'-hydroxy-1'-napthyl moiety substituted in the 3'-position with a group,

wherein $R^I$ is perhalomethyl and $R^{II}$ is hydrogen or perhalomethyl; B is a phenyl moiety substituted with an electron-donating substituent; X' represents the atoms necessary to complete a ring-closing moiety selected from a sulfamphthalein moiety and a sulfamnaphthalein moiety; and Z is a carbonyl moiety possessing a

group bonded to said N atom of said ring-closing moiety that undergoes an irreversible cleavage reaction in alkaline solution above a predetermined alkaline pH, said B moiety being sufficiently electron donating to give a compound having an epsilon of at least 4000 in the visible wavelength range as measured in trifluoroethanol;

(b) contacting said silver halide layer(s) and said light-screening dye with a processing composition having an alkaline pH above said predetermined pH;

(c) effecting thereby development of said silver halide layer(s);

(d) maintaining the pH of said processing composition in contact with said light-screening dye above said predetermined alkaline pH for a time sufficient to effect irreversible cleavage of said Z moiety whereby said colored light-screening dye is converted to a colorless compound;

(e) forming as a result of said development, an imagewise distribution of diffusible image dye-providing material; and (f) transferring, by diffusion, at least a portion of said imagewise distribution of diffusible image dye-providing material to said image-receiving layer to provide a transfer image thereto.

38. A photographic process as defined in claim 37 wherein said light-screening dye is so positioned that exposure of said silver halide layer(s) is effected therethrough.

39. A photographic process as defined in claim 38 wherein said second support is transparent and said image-receiving layer and said light-screening dye are carried by said transparent second support of said second sheet-like element.

40. A photographic process as defined in claim 39 wherein said light-screening dye is disposed in said image-receiving layer.

41. A photographic process as defined in claim 39 wherein said first support is opaque.

42. A photographic process as defined in claim 37 wherein said product includes means providing a layer of a white pigment between said image-receiving layer and said silver halide emulsions.

43. A photographic process as defined in claim 42 wherein said means providing a layer of a white pigment comprises including a pigment dispersed in said processing composition.

44. A photographic process as defined in claim 42 wherein said means providing a layer of a white pigment comprises a preformed layer of a white pigment.

45. A photographic process as defined in claim 37 wherein each said image dye-providing materials is an image dye-providing material selected from image dyes and image dye intermediates.

46. A photographic process as defined in claim 45 wherein each said image dye-providing material is a dye.

47. A photographic process as defined in claim 46 wherein each said dye is a dye developer.

48. A photographic process as defined in claim 37 wherein said first and second sheet-like elements are in superposed relationship.

49. A photographic product as defined in claim 37 wherein said second sheet-like element is adapted to be superposed with said first sheet-like element.

50. A photographic process as defined in claim 37 wherein said light-screening dye is a compound of the formula

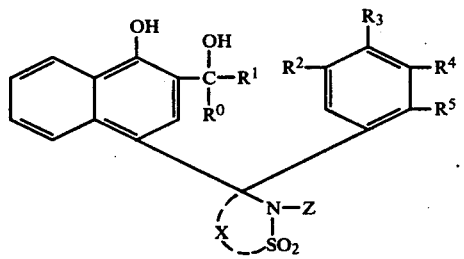

wherein $R^0$ is perhalomethyl selected from trifluoromethyl, difluoromethyl, difluorochloromethyl, dichlorofluoromethyl, dichloromethyl and trichloromethyl; $R^1$ is selected from hydrogen and perhalomethyl having the same meaning given above; $R^2$ and $R^4$ each are selected from hydrogen, alkyl, alkoxy, chloro and fluoro; $R^5$ is hydrogen, hydroxy, alkyl or alkoxy; $R^3$ is pyrrolidino, -N,N-(dialkyl)amino, -N,N-(w-$R^6$-alkyl)$_2$amino wherein $R^6$ is halo or hydroxy; $R^2$, $R^3$ and $R^4$ taken together represent the atoms necessary to complete a fused [ij]quinolizidine ring; X represents the atoms necessary to complete 2,3-dihydrobenz[d]isothiazole-1,1-dioxide or 2,3-dihydronaphtho[1,8-de]-1,2-thiazine-1,1-dioxide and Z is

wherein Y is an electron-withdrawing group.

51. A photographic process as defined in claim 50 wherein said light-screening dye is the compound having the formula

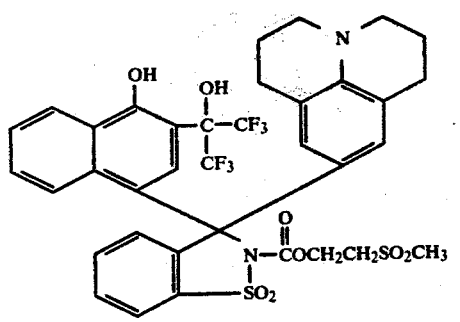
* * * * *